United States Patent
Khine et al.

(10) Patent No.: US 11,839,453 B2
(45) Date of Patent: Dec. 12, 2023

(54) SOFT CAPACITIVE PRESSURE SENSORS

(71) Applicant: THE REGENTS OF THE UNIVERSITY OF CALIFORNIA, Oakland, CA (US)

(72) Inventors: Michelle Khine, Irvine, CA (US); Joshua Kim, Irvine, CA (US); Gregory Washington, Irvine, CA (US); Theron Frederick Lee Smith, Irvine, CA (US); Floranne Tavailau Ellington, Irvine, CA (US); Joseph Garcia, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 902 days.

(21) Appl. No.: 16/678,626

(22) Filed: Nov. 8, 2019

(65) Prior Publication Data

US 2020/0069193 A1     Mar. 5, 2020

Related U.S. Application Data

(63) Continuation-in-part of application No. 15/474,937, filed on Mar. 30, 2017, now Pat. No. 10,898,084.
(Continued)

(51) Int. Cl.
*A61B 5/022*     (2006.01)

(52) U.S. Cl.
CPC ...... *A61B 5/022* (2013.01); *A61B 2562/0247* (2013.01)

(58) Field of Classification Search
CPC ......... A61B 5/021; A61B 5/022; A61B 5/024; A61B 5/02438; A61B 5/0245;
(Continued)

(56) References Cited

U.S. PATENT DOCUMENTS

| | | |
|---|---|---|
| 5,079,535 A | 1/1992 | Neuman |
| 5,111,826 A | 5/1992 | Nasiff |

(Continued)

FOREIGN PATENT DOCUMENTS

| | | |
|---|---|---|
| CN | 103219066 A | 7/2013 |
| JP | 2008-168032 A | 7/2008 |

(Continued)

OTHER PUBLICATIONS

A. Tuna, O. K. Erden, Y. D. Gokdel and B. Sarioglu, "3D printed capacitive pressure sensor with corrugated surface," 2017 13th Conference on Ph.D. Research in Microelectronics and Electronics (PRIME), 2017, pp. 149-152, doi: 10.1109/PRIME.2017.7974129.*

(Continued)

*Primary Examiner* — Ahmed M Farah
(74) *Attorney, Agent, or Firm* — NGUYEN TARBET LLC

(57) ABSTRACT

Soft capacitive pressure sensors for continuous wearable health monitoring applications are described herein. Wrinkled gold thin films on elastomeric substrates are used as robust parallel plate electrodes to create a robust integration with the polymer, allowing repeated normal force to deform the thin film without failure. By incorporating micro-ridged structures that support the counter electrodes to create air cavities within the elastomeric dielectric layer, pressure sensitivity is further increased. The pressure sensors are configured to measure human physiological signals such as pressure exerted from a radial pulse on a skin's surface. The radial pulse pressure detected by the sensor can be correlated to an arterial blood pressure. Calibration of said pressure sensors using a neural network allows for determination of absolute blood pressure.

14 Claims, 11 Drawing Sheets
(11 of 11 Drawing Sheet(s) Filed in Color)

Related U.S. Application Data

(60) Provisional application No. 62/875,418, filed on Jul. 17, 2019, provisional application No. 62/757,329, filed on Nov. 8, 2018, provisional application No. 62/316,375, filed on Mar. 31, 2016.

(58) Field of Classification Search
CPC .... A61B 2562/0247; A61B 2562/0261; A61B 2562/085; A61B 2562/14; A61B 2562/16; A61B 5/68; A61B 5/6801; A61B 5/6824
USPC .......................................................... 600/301
See application file for complete search history.

(56) References Cited

U.S. PATENT DOCUMENTS

| | | | |
|---|---|---|---|
| 5,494,043 | A | 2/1996 | O'Sullivan et al. |
| 5,533,511 | A * | 7/1996 | Kaspari .............. A61B 5/02007 600/494 |
| 6,595,742 | B2 | 7/2003 | Scimone |
| 10,161,737 | B2 * | 12/2018 | Pegan ........................ G01B 7/20 |
| 10,568,579 | B2 * | 2/2020 | Yi ........................ A61B 5/1036 |
| 2002/0130673 | A1 | 9/2002 | Pelrine et al. |
| 2005/0080349 | A1 | 4/2005 | Okada et al. |
| 2006/0169989 | A1 | 8/2006 | Bhattacharya et al. |
| 2006/0283262 | A1 | 12/2006 | Smits et al. |
| 2008/0119896 | A1 | 5/2008 | Wong et al. |
| 2011/0137577 | A1 | 6/2011 | Chen |
| 2011/0203390 | A1 * | 8/2011 | Tao ........................ G06F 3/0414 73/862.046 |
| 2011/0253288 | A1 | 10/2011 | Xie |
| 2011/0278040 | A1 | 11/2011 | Zhang et al. |
| 2012/0035508 | A1 | 2/2012 | Van Leer |
| 2012/0062245 | A1 * | 3/2012 | Bao ........................ H01L 29/84 324/661 |
| 2012/0086433 | A1 | 4/2012 | Cheng et al. |
| 2012/0121870 | A1 | 5/2012 | Toury et al. |
| 2013/0140611 | A1 | 6/2013 | Kim et al. |
| 2013/0264912 | A1 | 10/2013 | Kwon et al. |
| 2013/0281861 | A1 | 10/2013 | Flomerfelt et al. |
| 2013/0312541 | A1 | 11/2013 | Majidi et al. |
| 2014/0054599 | A1 | 2/2014 | Choi et al. |
| 2014/0290376 | A1 | 10/2014 | Rahajandraibe |
| 2015/0034237 | A1 | 2/2015 | Biggs et al. |
| 2015/0263235 | A1 | 9/2015 | Shin et al. |
| 2015/0294805 | A1 | 10/2015 | Hayward et al. |
| 2015/0366518 | A1 * | 12/2015 | Sampson ............. A61B 5/0205 600/509 |
| 2017/0020413 | A1 * | 1/2017 | Otaka ........................ G01B 7/22 |
| 2017/0086686 | A1 | 3/2017 | Narasimhan et al. |
| 2017/0281082 | A1 | 10/2017 | Khine et al. |
| 2018/0116534 | A1 * | 5/2018 | Tal ........................ A61B 5/7267 |
| 2018/0225990 | A1 * | 8/2018 | Jiang ........................ G09B 23/28 |
| 2018/0303434 | A1 | 10/2018 | Selvara |

FOREIGN PATENT DOCUMENTS

| | | | |
|---|---|---|---|
| WO | 2014066802 | A1 | 5/2014 |
| WO | 2015179320 | A1 | 11/2015 |
| WO | 2018144772 | A1 | 2/2018 |

OTHER PUBLICATIONS

Shao Y, Zhang Q, Zhao Y, Pang X, Liu M, Zhang D, Liang X, "Flexible Pressure Sensor with Micro-Structure Arrays Based on PDMS and PEDOT:PSS/PUD&CNTs Composite Film with 3D Printing," Materials (Basel). Oct. 29, 2021;14(21):6499. doi: 10.3390/ma14216499. PMID: 34772026; PMCID: PMC8585123.*

Fu, J., Zhu, T., Liang, Y. et al. "Fabrication of capacitive pressure sensor using single crystal diamond cantilever beam," Sci Rep 9, 4699 (2019). https://doi.org/10.1038/s41598-019-40582-x.*

Mannsfeld et al., Highly sensitive flexible pressure sensors with microstructured rubber dielectric layers Nat. Mater, 2010, 9, 859.

Y. Joo, J. Byun, N. Seong, J. Ha, H. Kim, S. Kim, T. Kim, H. Im, D. Kim, Y. Hong, Nanoscale 2015, 7, 6208.

X. Shuai, P. Zhu, W. Zeng, Y. Hu, X. Liang, Y. Zhang, R. Sun, C. P. Wong, ACS Appl. Mater. Interfaces 2017, 9, 26314.

J. Wang, J. Jiu, M. Nogi, T. Sugahara, S. Nagao, H. Koga, P. He, K. Suganuma, Nanoscale 2015, 7, 2926.

N. Luo, W. Dai, C. Li, Z. Zhou, L. Lu, C. C. Y. Poon, S. C. Chen, Y. Zhang, N. Zhao, Adv. Funct. Mater. 2016, 26, 1178.

J. Kim, S.-J. J. Park, T. Nguyen, M. Chu, J. D. Pegan, M. Khine, Appl. Phys. Lett. 2016, 108, 061901.

J. D. Pegan, J. Zhang, M. Chu, T. Nguyen, S.-J. Park, A. Paul, J. Kim, M. Bachman, M. Khine, Nanoscale 2016, 8, 17295.

B.-J. Park, J. Kim, M. Chu, M. Khine, Adv. Mater. Technol. 2016, 1, 1600053.

C.-S. Chen, D. N. Breslauer, J. I. Luna, A. Grimes, W.-C. Chin, L. P. Lee, M. Khine, 2008, DOI 10.1039/b719029h.

Bandodkar, A.J., and Wang, J. 2014. "Non-invasive wearable electrochemical sensors: a review" Trends Biotechno/32: 363-371.

Biagiotti, V. et al. 2012 "Probe accessibility effects on the performance of electrochemical biosensors employing DNA monolayers" Anal. Bioanal. Chem. 402: 413-421.

Drelich, J. and Chibowski, E. 2010 "Superhydrophilic and superwetting surfaces: Definition and mechanisms of control" Langmuir 26: 18621-18623.

Freschauf, L.R. et al. 2012 "Shrink-induced superhydrophobic and antibacterial surfaces in consumer plastics" PLoS One 7: e40987 (in 7 pages).

Fu et al. 2009 "Tunable nanowrinkles on shape memory polymer sheets" Adv Mater 21 : 4472-4476.

Gabardo, C. et al. 2013 "Bench-top fabrication of hierarchically structured high surface-area electrodes" Adv. Funct. Mater. 23: 3030-3039.

Gabardo, C.M. et al. 2015 "Rapid prototyping of microfluidic devices with integrated wrinkled gold micro-/nano textured electrodes for electrochemical analysis" Analyst 140: 5781-5788.

Hauke et al. 2017 "Superwetting and aptamer functionalized shrink-induced high surface area electrochemical sensors" Biosensors and Bioelectronics 94: 438-442.

Heikenfeld, J., 2016 "Non-invasive analyte access and sensing through eccrine sweat: challenges and outlook circa 2016" Electroanalysis 28: 1242-1249.

Kimmel, D.W. et al. 2012 "Electrochemical sensors and biosensors" Anal. Chem. 84: 685-707.

Lubin, A.A. and Plaxco, K.P., 2010 "Folding-based electrochemical biosensors: the case for responsive nucleic acid architectures" Acc. Chem. Res. 43: 496-505.

Pegan, J.D. et al. 2013 "Flexible shrink-induced high surface area electrodes for electrochemiluminescent sensing" Lab Chip 13: 4205-4209.

Pheeny, C.G. and Barton, J.K. 2012 "DNA electrochemistry with tethered methylene blue" Langmuir 28: 7063-7070.

Rowe, A.A. et al. 2010 "Reagentless measurement of aminoglycoside antibiotics in blood serum via an electrochemical, ribonucleic acid aptamer-based biosensor" Anal. Chem. 82: 7090-7095.

Salvarezza, R.C. et al. 1990 "Monte Carlo simulation applicable to the growth of rough metal overlayers: parametric relationships related to the electrochemical roughening" Phys. Rev. B 41: 502-512.

Setia, U. and Gross, P.A. 1976 "Administration of tobramycin and gentamicin by the intravenous route every 6 h in patients with normal renal function" J. Infect. Dis. 134: S125-129.

Sonney, S. et al. 2015 "Rapid bench-top fabrication of poly(dimethylsiloxane), polystyrene microfluidic devices incorporating high-surface area sensing electrodes" Biomicrofluidics 9: 026501 (in 11 pages).

Ausman et al. 2000 "Organic Solvent Dispersions of Single-Walled Carbon Nanotubes: Toward Solutions of Pristine Nanotubes" J Phys Chem B 104: 8911-8915.

Byun I. et al. 2013 "Transfer of thin Au films to polydimethylsiloxane (PDMS) with reliable bonding 2 using (3-mercaptopropyl)trimethoxysilane (MPTMS) as a molecular adhesive" J Micromech Microeng 23(8): 1-10.

(56) References Cited

OTHER PUBLICATIONS

Chirinos, J. A. et al. 2011 "Ethnic differences in arterial wave reflections and normative equations for augmentation index" Hypertension 57: 1108-1116.
Li et al. 2012 "Dispersion of Carbon Nanotubes in Organic Solvents Initiated by Hydrogen Bonding Interactions" AIChE Journal 58: 2997-3002.
Lipomi et al. 2011 "Skin-like pressure and strain sensors based on transparent elastic films of carbon nanotubes" Nature Nanotechnology 6: 788-792.
Nelson et al., 2010 "Noninvasive Measurement of Central Vascular Pressures With Arterial Tonometry: Clinical Revival of the Pulse Pressure Waveform?" Mayo Clin Proc 85(5): 460-472.
Schwartz et al. (2013 "Flexible polymer transistors with high pressure sensitivity for application in electronic skin and health monitoring" Nature Communications 4: 1859 (in 8 pages).
Wang et al. 2014 "Silk-Molded Flexible, Ultrasensitive, and Highly Stable Electronic Skin for Monitoring Human Physiological Signals" Advanced Materials 26: 1336-1342.
Zhuo et al. "High sensitivity flexible capacitive pressure sensor using polydimethylsiloxane elastomer dielectric layer microstructured by 3-D printed mold." IEEE Journal of the Electron Devices Society 5.3 (2017): 219-223.

\* cited by examiner

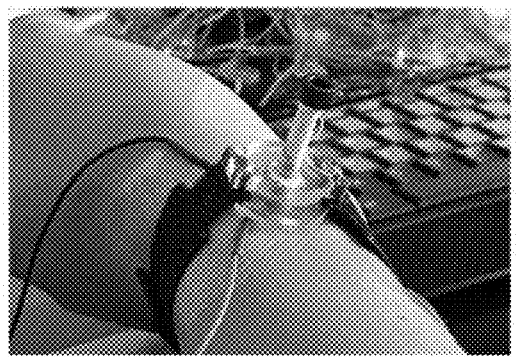
FIG. 13A
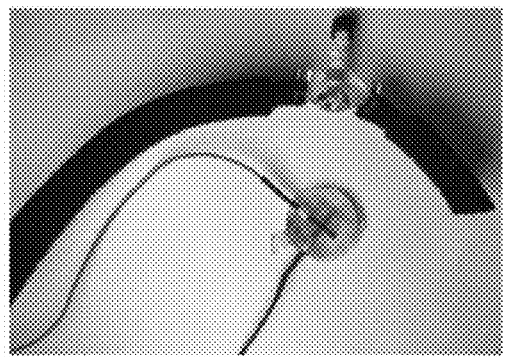
FIG. 13B
FIG. 14
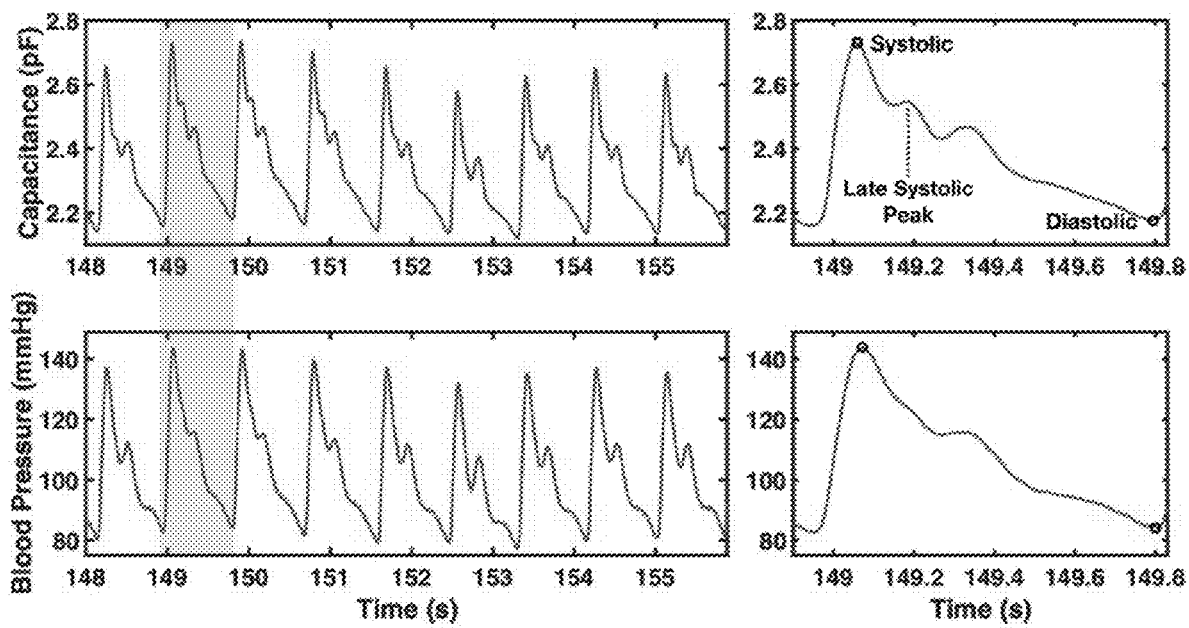
FIG. 15A
FIG. 15B

SOFT CAPACITIVE PRESSURE SENSORS

CROSS-REFERENCES TO RELATED APPLICATIONS

This application is a non-provisional and claims benefit of U.S. Provisional Application No. 62/757,329 filed Nov. 8, 2018 and U.S. Provisional Application No. 62/875,418 filed Jul. 17, 2019, the specification(s) of which is/are incorporated herein in their entirety by reference.

This application is a continuation-in-part and claims benefit of U.S. application Ser. No. 15/474,937 filed Mar. 30, 2017, which is a non-provisional and claims benefit of U.S. Provisional Application No. 62/316,375 filed Mar. 31, 2016, the specification(s) of which is/are incorporated herein in their entirety by reference.

BACKGROUND OF THE INVENTION

Field of the Invention

The present invention relates to medical devices for blood pressure reading. More specifically, the present invention relates to flexible and stretchable capacitive based pressure sensors for continuous wearable health monitoring applications. Further still, the present invention relates to neural network calibration of pressure sensors for continuous pressure readings.

Background Art

The arterial pulse contains a wealth of cardiovascular information, including systolic and diastolic pressures that have clinically been used to quantitatively evaluate and monitor cardiovascular diseases as well as general health. These arterial pulses can be measured in many different locations of the body, such as the brachial and radial artery, using non-invasive blood pressure (NIBP) monitoring tools. Studies have indicated that monitoring blood pressure fluctuations throughout the day can provide insight on cardiovascular health. For this reason, there is a need to continuously monitor blood pressure to better understand blood pressure variability and its effect on cardiovascular health.

Oscillometric measurements, using inflatable brachial arm cuffs, have become widely used in the clinical setting, but are intermittent and only provide one systolic and diastolic blood pressure value over a duration of approximately 30-40 seconds. Alternatively, continuously monitoring beat-to-beat blood pressure requires detection and analysis of each cardiac cycle as it pulses to peripheral arteries. The finger cuff volume-clamp method is one such method capable of measuring beat-to-beat blood pressure, but currently does not have the form factor to enable ambulatory monitoring.

Arterial applanation tonometry is another NIBP method that uses a pressure sensor, often a hand-held probe, to locally flatten (applanate) an artery. Subsequently, the arterial pressure is measured by adjusting the degree of arterial applanation. Applanation tonometry greatly depends on the operator to consistently position the pressure transducer on the artery to measure pulse pressure which is not amenable for ambulatory continuous monitoring. Newer alternative methods use soft sensors that are capable of improving conformability to the body. Conformability improves the coupling between the sensor and body allowing for more accurate measurements of the arterial pulse. However, current reported soft sensors measure pulse transit times between two points as a means to calculate beat-to-beat blood pressure using theoretical models and not from the amplitude changes of the pulse pressure waveforms. Moreover, there is a need to develop highly sensitive pressure sensors that can detect small pressures (<5 kPa; approximate pressure on the surface of the skin exerted by the radial pulse from a healthy subject) and characterized with high response times (~100 ms; approximate time between the diastolic and systolic points in a radial artery pulse wave).

Capacitive pressure sensors have gained much attention due to their simple device design, quick response times, relatively low hysteresis, and low power consumption requirements which are all highly desirable for soft wearable electronic applications. When soft dielectric materials are used, compression of the dielectric layer leads to an increased capacitance which is equal to:

$$C = \varepsilon_o \varepsilon_r \frac{A}{d} \quad (1)$$

where $\varepsilon_o$ is the permittivity of vacuum, $\varepsilon_r$ is the relative permittivity of the dielectric material. A is the surface area overlap of the parallel plate electrodes, and d is the distance between the parallel plate electrodes.

Capacitive sensors can be configured to "map" pressures with multiplexing data acquisition tools. For example, a grid of capacitive sensors may spatially resolve localized pressure on a surface. The simple layout for capacitive sensors makes it an attractive modality for detecting mechanical pressure. However, current capacitive sensors are typically characterized with low pressure sensitivities (less than or equal to about 0.5-1 $kPa^{-1}$) due to the small compression of the dielectric layer which impacts arterial pulse measurements and have not been used for long term studies (>30 seconds) to reliably detect radial pulse.

Previously reported capacitive sensors often use stiff substrates (i.e. polyethyelene (PET)) which may limit its applications for detecting radial artery pulse. For example, PET substrates are stiff which may inhibit conformal contact to the human body. Also, a stiff substrate may delocalize the stress over a larger area which may dampen the signal. This may have detrimental effects in acquiring reliable data as well as mapping capabilities for spatial resolution. Another limitation is the durability of the electrodes used to develop prior capacitive sensors. These electrodes were brittle and cannot withstand large bending/tensile/torsion strains. Other previously reported skin-like capacitive pressure sensors using elastic carbon nanotube (CNT) conductors supported on polydimethylsiloxane (PDMS) substrates had low pressure sensitivities which would have made it difficult to measure arterial pulse pressures. Other types of capacitive pressure sensors incorporate PDMS micro-pyramidal structures in the dielectric layer to significantly improve pressure sensitivities, or micro-hairy PDMS structures to improve conformability to the surface of the skin subsequently amplifying arterial pulse pressure measurements. These sensors have demonstrated that by applying more pressure down on the sensor into the skin, they were able to achieve slightly larger changes in the radial arterial pulse pressure waveform. However, these changes were minimal, possibly suggesting that the dynamic range of the pressure sensors were not sufficient for applanation tonometry.

BRIEF SUMMARY OF THE INVENTION

It is an objective of the present invention to provide sensitive mechanical pressure sensors and method of producing said sensors for measuring human physiological signals such as the pressure exerted from the radial pulse on the surface of the epidermis (skin), as specified in the independent claims. Furthermore, accurate calibration of said sensors for continuous monitoring of pulsatile blood flow is described herein. Embodiments of the present invention are given in the dependent claims and can be freely combined with each other if they are not mutually exclusive.

Arterial applanation is a critical component to achieving consistent pulse pressure measurements by reducing the elastic resistance (i.e. skin) between the pressure sensor and the artery. To achieve arterial applanation and consistent pulse pressure measurements requires the pressure sensor to have high pressure sensitivities over a wide dynamic range. One such way to achieve a wide dynamic range in soft capacitive pressure sensors includes creating air gaps with micro-ridged structures.

In some aspects, the present invention features soft capacitive pressure sensors that incorporate wrinkled metallic thin films to develop soft stretchable electrodes for radial tonometry applications. For instance, the capacitive pressure sensors can measure and monitor pulsatile blood flow. Parallel plates of the sensor can be brought closer together when the radial artery induces pressure on the sensor. The wrinkled structures of the thin film create robustness for the thin film to repeatedly flex. This enables continuous arterial pulse pressure measurements with enough sensitivity over a large dynamic range and fast response times of less than 10 ms to capture the details of the pulse pressure waveform.

Highly wrinkled thin films provide mechanical robustness to mechanical strains when supported on soft elastomeric substrates. Due to the soft nature of these electrodes, it is possible for the sensors to conform to the body and accurately measure pressure from an arterial pulse. To increase pressure sensitivity and dynamic range, micro-ridged structures were included in the dielectric layer to improve pressure sensitivities of up to 5-fold within a wide pressure range from 0-10 kPa. These microstructures lift up the counter electrode to create an air cavity in the dielectric layer, thereby increasing the amount the dielectric layer can be compressed. In effect, this reduces the elastic resistance in the dielectric layer. The effective dielectric permittivity is also lowered due to the presence of an air cavity ($e_{air}=1$). When the dielectric layer is compressed, the effective dielectric permittivity increases as the air cavity volume decreases leading to larger changes in capacitance. Continuous measurements of beat-to-beat blood pressure with these soft capacitive pressure sensors are demonstrated by comparing against an FDA approved NIBP monitoring device.

In some embodiments, the capacitive pressure sensor may comprise a first electrode layer, a second electrode layer, a dielectric layer disposed on the first electrode layer such that the dielectric layer is between the first and second electrode layers, and one or more elastic ridges projecting from the second electrode layer toward the dielectric layer and first electrode layer. The one or more elastic ridges create an air gap that separates the first electrode layer and the second electrode layer. When the sensor is in a resting configuration, the air gap is disposed between the first electrode layer and the second electrode layer. The air gap functions as a second dielectric layer. When the sensor is compressed, the first electrode layer and the second electrode layer are brought closer to each other, thereby reducing a height of the air gap and increasing a pressure sensitivity and capacitance of the sensor. In one embodiment, the first electrode layer may comprise an elastomer layer and a conductive metallic film disposed between the elastomer layer and the dielectric layer. In another embodiment, the second electrode layer may comprise an elastomer layer and a conductive metallic film disposed on the elastomer layer. In a non-limiting example, the elastomer layers may comprise polydimethylsiloxane. The conductive metallic films may comprise a wrinkled Au thin film. The dielectric layer may comprise a soft silicone rubber. In some embodiments, a pressure sensitivity of the sensor ranges from about 0.1 $kPa^{-1}$ to about 0.2 $kPa^{-1}$ in a pressure range between 0-10 kPa. A response time of the sensor is less than about 20 ms, preferably less than 10 ms.

In some embodiments, the conductive layer may be any thin film metal and is not limited to Au. Other examples include copper, silver, or aluminum thin films. In other embodiments, the electrode layer may comprise wrinkled percolating network carbon nanotube thin films. In some embodiments, the elastomer layer may comprise a silicon-based material or a non-silicon material, such as polyurethanes. In other embodiments, the silicone dielectric material may be replaced with other dielectric materials including, hut not limited to, lead zirconate titanate, barium titanate, polyvinylidene fluoride, or an oxide of zirconia, titania, or silica.

In some aspects, the present invention also provides a method to, fabricate stretchable and flexible electrodes that can be assembled to create soft capacitive based sensors for continuous blood pressure monitoring applications. According to some embodiments, the method of fabricating a capacitive pressure sensor may comprise attaching a conductive metallic film to a silicone elastomer layer to form a first electrode layer, attaching a dielectric layer to the first electrode layer such that the conductive metallic film is disposed between the silicone elastomer layer and the dielectric layer, attaching a second conductive metallic film to a second silicone elastomer layer to form a second electrode layer, the silicone elastomer layer having one or more elastic ridges projecting from its surface, and attaching the first electrode layer to the second electrode layer such that the one or more elastic ridges are directed towards the dielectric layer and first electrode layer. The elastic ridges are configured to create an air gap between the first electrode layer and the second electrode layer, e.g. the elastic ridges push or separate the dielectric layer and first electrode layer away from the second electrode layer. However, when the sensor is compressed, e.g. by the arterial pulses, the first electrode layer and the second electrode layer are brought closer to each other, thereby reducing a height of the air gap and increasing a pressure sensitivity and capacitance of the sensor.

In some embodiments, the fabrication method may include molding the silicone elastomer layer to have the one or more elastic ridges projecting from its surface. In other embodiments, the fabrication method may further comprise calibrating the capacitive pressure sensor using an artificial neural network (ANN). The calibration step may comprise generating a calibration model by training the ANN using a training set comprised of measured blood pressure signals and one or more biological input variables. These sensors are able to withstand tensile/bending/torsion strains, improving durability while also maintaining a soft mechanical nature for conformal contact to the human body. Soft capacitive sensors described here also possess pressure sensitivities of about 0.1 $kPa^{-1}$-0.2 $kPa^{-1}$ in a pressure range between 0-10 kPa with quick response times (<20 ms).

One of the unique and inventive technical features of the present invention is the ridges that support the counter electrode such that an air gap is formed between the two electrode layers. In addition, the present invention has the feature of the ridges and dielectric layer being separate components. The dielectric layer is comprised of both an air gap and the dielectric material used. When both of these are present, the dielectric constant is a combination of these two. The dielectric constant of air is equal to 1, whereas a silicone elastomer, such as PDMS, is about 3. Therefore, the dielectric constant of the sensor is e in between depending on the proportion of volume each of these occupies. When the pressure sensor is compressed, the air gap volume is reduced, which leads to an increase dielectric constant closer to 3. Without wishing to limit the invention to any theory or mechanism, by separating the ridge from the dielectric layer, the increased dielectric constant contributed to higher pressure sensitivity. The inventive technical features of the present invention surprising resulted in producing sensors that are highly sensitive over a wide pressure range and allow for accurate measurement of beat to beat blood pressure in the arterial pulse. None of the presently known prior references or works has the unique inventive technical feature of the present invention.

Furthermore, the prior works teach away from the present invention. For example, previous sensors utilized dielectric materials formed to contain an array of structures. However, the advantageous strategy of the present invention to increase the dielectric constant and increase pressure sensitivity cannot be implemented if the dielectric layer is microstructured.

In some embodiments, having two ridges is advantageous over an array of structures because the two ridges allow for easy fabrication whereas fabrication of the array of structures requires etching silicon wafers, which is a time consuming process and does not always produce high fidelity. Compression of an array of dielectric structures lead to mechanical resistance as it is further compressed, e.g., as air gap volume decreases, the amount of material that needs to be compressed increases. Compression of two ridges requires less mechanical force and virtually eliminates the compression of the dielectric material, thus improving pressure sensitivity.

According to other embodiments, the present invention provides a method for monitoring blood pressure in a subject may comprise providing a capacitive pressure sensor, attaching the sensor to a forearm or wrist of the subject at the radial artery, measuring a blood pressure signal of the subject using the sensor, where pulsing of the radial artery causes compression of the sensor, which detects the blood pressure signal corresponding to the radial artery pulses, and determining an absolute blood pressure value from the measured signal using a calibration model. In one aspect, blood pressure can be monitored continuously. In further embodiments, the method includes calibrating the capacitive pressure sensor using an artificial neural network (ANN). This calibration step may comprise measuring a plurality of blood pressure signals from the subject, measuring one or more biological input variables from the subject, combining the measured blood pressure signals and the biological input variables to form a training set, and training the ANN using the training set to generate the calibration model.

Hence, the present invention allows for the automated calibration of arterial blood pressure for continuously monitoring beat-to-beat blood pressure non-invasively. In one embodiment, the capacitive sensors may be calibrated to the FDA approved ClearSight® device. Alternatively, in order to output mmHg without the ClearSight® device, a neural network has been developed to input various parameters. In a non-limiting embodiment, the neural network may be trained using various inputs that make up the training set, such as capacitance measurements from the sensors, pressure applied from the mechanical sensors, pulse rate, EKG, accelerometer data, gyroscope data, magnetometer data, hemodynamic monitoring data, and ClearSight® data to create a model. The training set comprising measurements of blood pressure signals and one or more biological input variables may be obtained from multiple subjects. After this robust model is created, inputting the capacitance measurements from the sensors outputs the absolute pressure. Motion artifacts may also be subtracted out using this approach by having the subjects for the model move in pre-defined, known ways while generating the training set. When the calibrated sensor is applied to the same person, the pulse waveform measured by the sensor may be correlated to arterial blood pressure, thus accurate blood pressure readings may be obtained without any other inputs. For instance, no additional equipment by the end user is required once the sensor is calibrated; the user simply places the pressure sensor on the radial artery and absolute mmHg will register.

Another unique and inventive technical feature of the present invention is the use of the neural network to calibrate a continuous mechanical blood pressure sensor. Without wishing to limit the invention to any theory or mechanism, it is believed that the technical feature of the present invention advantageously provides for non-invasive monitoring of beat-to-beat blood pressure. None of the presently known prior references have the unique inventive technical feature of the present invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWINGS

This patent application contains at least one drawing executed in color. Copies of this patent or patent application publication with color drawings will be provided by the Office upon request and payment of the necessary fee.

The features and advantages of the present invention will become apparent from a consideration of the following detailed description presented in connection with the accompanying drawings in which:

In FIG. 1A, an air gap is formed due to the presence of ridges along the trace edge of the electrode. In FIG. 1B, when compressed, the air gap area is reduced, thereby changing the effective dielectric constant. The distance between the electrodes is also reduced, thereby increasing capacitance.

FIG. 10A shows PS curves of seven different capacitive sensors with micro ridge structures (85 µm height; 100 µm width). FIG. 10B is an inset of the PS curves of FIG. 10A from 0-10 kPa. FIG. 10C shows PS curves of three different sensors with larger micro ridge (190 µm height; 600 µm width). FIG. 10D is an inset of the PS curves of FIG. 10C from 0-10 kPa. FIG. 10E shows PS curved of three different sensors without micro ridge structures. FIG. 10F is an inset of the PS curves of FIG. 10E from 0-10 kPa.

FIG. 12A shows the signal response from pressure sensor when induced with cyclic strain. FIG. 12B shows the Fast Fourier transform (FFT) of applied cyclic strain and signal response of the pressure sensor measured at ~11 Hz.

FIG. 13A shows a setup of how the pressure sensor is attached to the wrist for measuring radial artery pulse.

FIG. 13B shows the pressure sensor and wrist attachment components of the setup in FIG. 13A.

FIG. 14 shows a photographic image of where sensors were placed during beat-to-beat blood pressure measurements.

FIG. 15A shows an example of arterial pulse waveforms measured by the capacitive pressure sensor (top row) and the ClearSight® device (bottom row).

FIG. 15B shows one pulse waveform indicating cardiovascular features from the highlighted section of FIG. 15A.

DETAILED DESCRIPTION OF THE INVENTION

Following is a list of elements corresponding to a particular element referred to herein:

| | |
|---|---|
| 100 | capacitive pressure sensor |
| 110 | first electrode layer |
| 120 | second electrode layer |
| 112, 122 | elastomer layer |
| 114, 124 | conductive film |
| 125 | ridges |
| 130 | dielectric layer |
| 140 | air gap |

Figure 1A:
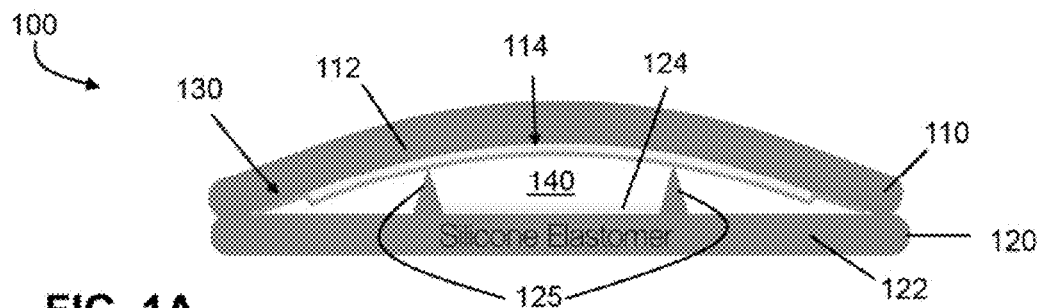
FIGS. 1A-1B show a cross-sectional view of a capacitance pressure sensor of the present invention. A dielectric layer is disposed between two wrinkled Au thin film (wAu) layers.
Figure 1B:
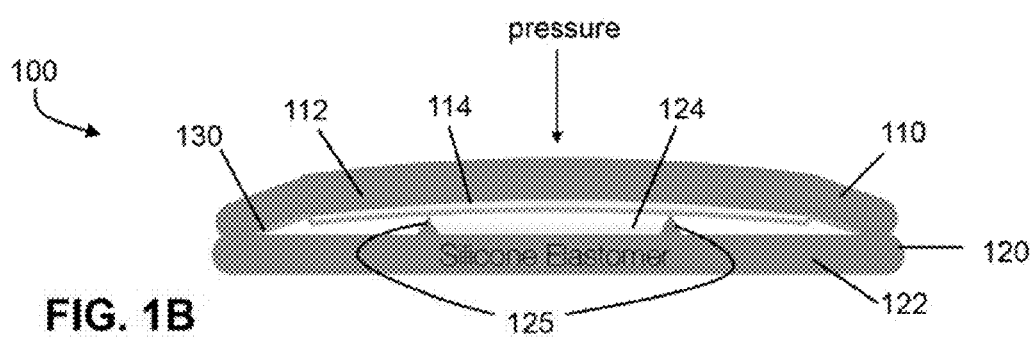

Referring now to FIGS. 1A-1B, in some embodiments, the present invention features a capacitive pressure sensor (100). The sensor (100) may comprise a first electrode layer (110), a second electrode layer (120), and a dielectric layer (130) juxtaposed between the first and second electrode layers (110, 120). When the sensor (100) is in a resting configuration as shown in FIG. 1A, an air gap (140) is disposed between the first electrode layer (110) and the second electrode layer (120). The air gap (140) can act as a second dielectric layer. In preferred embodiments, the sensor (100) is bendable, compressible, and flexible. When the sensor (100) is compressed as shown in FIG. 1B, a height of the air gap is reduced, thereby bringing the first electrode layer (110) and the second electrode layer (120) closer to each other and increasing a pressure sensitivity and capacitance of the sensor. Without wishing to limit the invention to any theory or mechanism, it is believed that the present invention advantageously provides a pressure sensor with high electromechanical reliability, high pressure sensitivity, quick response times, and low energy consumption. None of the presently known prior references or work has the unique inventive technical feature of the present invention.

In some embodiments, the first electrode layer (110) may comprise an elastomer layer (112) and a conductive film (114) disposed on the elastomer layer (112). The dielectric layer (130) may be disposed on the conductive film (114) of the first electrode layer (110). In other embodiments, the second electrode layer (120) may comprise an elastomer layer (122) and a conductive film (124) disposed on the silicone elastomer layer (122). In further embodiments, the second electrode layer (120) may have elastic ridges (125) projecting from the second electrode layer (120) toward the first electrode layer (110), which creates the air gap that separates the first electrode layer (110) and the second electrode layer (120) in the resting configuration. In one embodiment, the conductive film (124) may be disposed between the elastic ridges (125). Preferably, the elastic ridges (125) can bend so as to reduce the height of the air gap when the sensor (100) is compressed. As used herein, the height of the air gap may refer to the distance between the dielectric layer (130) and the conductive film (124) of the second electrode layer (120).

In one embodiment, the elastic ridges (125) may comprise two ridges. The ridges may be parallel to each other on the second electrode layer (120). In other embodiments, the elastic ridges (125) may comprise more than two ridges. In some embodiments, the elastic ridges may be elongated strips having a triangular profile or cross-section as shown in the figures. The pointed distal end of the triangular ridge may be contacting the dielectric layer of the counter electrode layer. In other embodiments, the elastic ridges may have an upside down "U" profile. In some other embodiments, the elastic ridges may be pyramidal structures, for example, two pyramidal structures.

In some embodiments, the elastomer layer (112, 122) may comprise silicone such as polydimethylsiloxane. In other embodiments, the elastomer layer (112, 122) may comprise non-silicone elastomers such as polyurethane or the like.

In some other embodiments, the conductive film (114, 124) is a metallic film. The metallic film may be wrinkled, such as wrinkled Au thin film. Other conductive materials that may be used in accordance with the present invention include, but are not limited to, metals such as copper, silver, or aluminum thin film. Alternatively, percolating networks of conductive nano-materials may be used as conductive electrodes, such as carbon nanotubes.

In still other embodiments, the dielectric layer (130) may comprise a soft silicone rubber, such as Ecoflex. Thus, a dielectric constant of the sensor is about 1 when the sensor is in the resting configuration. When the sensor is compressed, the dielectric constant may be about 3. In some other embodiments, the dielectric layer (130) may comprise dielectric materials with higher dielectric constants. For instance, the dielectric constant of the dielectric material may be greater than 3. Examples of dielectrics with higher dielectric constants include, but are not limited to, oxides such as oxides of zirconia, titania, or silica, and piezoelectric materials such as lead zirconate titanate (PZT), Barium Titanate ($BaTiO_3$), polyvinylidene fluoride (PVDF). Without wishing to limit the present invention to a particular theory or mechanism, the dielectric material is selected such that the dielectric constant of said material is much larger than that of air, which is 1. This may allow for a greater change in the dielectric constant when the sensor is compressed, thus increasing the pressure sensitivity.

In one embodiment, a pressure sensitivity of the sensor may be about 0.1 $kPa^{-1}$ to about 0.2 $kPa^{-1}$ in a pressure range between 0-10 kPa. In another embodiment, a response time of the sensor is less than about 20 ms, preferably less than 10 ms.

According to some embodiments, the present invention features a method of monitoring blood pressure in a subject. The method may comprise providing any one of the capacitive pressure sensors (100) described herein, attaching the sensor to a forearm or wrist of the subject at the radial artery and operably connecting the sensor to a pressure gauge. Without wishing to limit the present invention to a particular theory or mechanism, the pulsing of the radial artery causes compression of the sensor, which detects a signal corresponding to the radial artery pulses and sends said signal to the pressure gauge. The pressure gauge can then determine, e.g. calculate, the blood pressure from said signal.

In yet another embodiment, the method of monitoring blood pressure in a subject may comprise attaching the capacitive pressure sensor (100) to a forearm or wrist of the subject at the radial artery, measuring a blood pressure signal of the subject using the sensor (100), where pulsing of the radial artery causes compression of the sensor and the sensor (100) detects the blood pressure signal corresponding to the radial artery pulses, and determining an absolute blood pressure value from the measured signal using a calibration model. In a further embodiment, the monitoring method may further comprise calibrating the capacitive pressure sensor (100) using an artificial neural network (ANN). The calibration step may comprise measuring a plurality of blood pressure signals from the subject, measuring one or more biological input variables from the subject, combining the measured blood pressure signals and the biological input variables to form a training set, and training the ANN using the training set to generate the calibration model. The calibration model is used to calibrate the sensor (100), which allows for the absolute blood pressure value to be determined from the measured signal. In other embodiments, the calibration step may further comprise subtracting out motion artifacts by including movement data in the training set. In some embodiments, the training set may comprise measurements of blood pressure signals and one or more biological input variables from multiple subjects. In other embodiments, the one or more biological input variables may comprise sensor pressure, pulse rate, EKG data, accelerometer data, gyroscope data, magnetometer data, or hemodynamic monitoring data.

In one example, a calibration model may utilize additional physiological parameters including pulse transit time (PTT). PTT is the time it takes for a blood pulse to go from one point to another. This can be measured by using an electrocardiogram (ECG) and a proximal sensor such as the pressure sensor on the radial artery. These two components can allow for the detection of the start of the pulse and how long that pulse takes to get to the radial artery. Higher pressure can send a pulse faster through the body, thus PTT may be correlated to blood pressure. PTT can be useful for calibrating the capacitive pressure sensor to a baseline. Combining PTT and capacitive sensor information can therefore be used to create an ANN to calibrate the pressure sensor.

In one embodiment, the sensor may be used to monitor the blood pressure of the subject continuously, e.g. beat to beat. In another embodiment, the sensor may also be used to take single blood pressure measurement. Preferably, the sensor car be used to monitor the blood pressure non-invasively. In some embodiments, the sensor (100) may be attached to the forearm or wrist by an adhesive or a cuff, such as an adjustable or elastic band.

According to other embodiments, the present invention features a method of fabricating a capacitive pressure sensor (100). The method may comprise attaching a conductive metallic film (114) to an elastomer layer (112) to form a first electrode layer (110), attaching a dielectric layer (130) to the first electrode layer (110) such that the conductive metallic film (114) is disposed between the elastomer layer (112) and the dielectric layer (130), attaching a second conductive metallic film (124) to a second elastomer layer (122) that has elastic ridges (120) projecting from its surface to form a second electrode layer (120), and attaching the first electrode layer (110) to the second electrode layer (120). Preferably, the elastic ridges (120) is directed towards the first electrode layer (110) and the dielectric layer (130) is juxtaposed between the first electrode layer (110) and the second electrode layer (120). The elastic ridges (125) thus create an air gap (140) between the first electrode layer (110) and the second electrode layer (120). When the sensor (100) is compressed, a height of the air gap is reduced, thereby bringing the first electrode layer (110) and the second electrode layer (120) closer to each other and increasing a pressure sensitivity and capacitance of the sensor.

In alternative embodiments, the present invention may have the ability to sense different areas by using a grid of these sensors. This is critical in being able to spatially resolve the optimal location of the radial artery. This can be accomplished by introducing additional electrodes in the fabrication process. It is understood that the invention is not limited to a 4×4 grid sensor, in other embodiments, the amount of sensing 'pixels' can be any size, instance 1×1, 2×2, 3×3, 5×5, 10×10, 100×100, etc. Alternatively or in conjunction, multiple sensors may be used together to enable mapping capabilities (spatial resolution). For example, 2-5 sensors may be operatively coupled to each other in order to sense different areas.

According to some other embodiments, the present invention features a method of calibrating a mechanical, continuous blood pressure monitor using an artificial neural network (ANN). As a non-limiting example, the method may comprise: providing a mechanical, continuous blood pressure monitor, applying the blood pressure monitor to a patient, measuring a plurality of mechanical blood pressure signals from the patient, measuring one or more additional biological input variables from the patient, combining the measured mechanical blood pressure signals and the additional biological input variables to form a training set, training the ANN using the training set to generate a calibration model, and calibrating the blood pressure monitor using the calibration model, such that the blood pressure monitor may be used to continuously measure a blood pressure of the patient.

In some embodiments, the blood pressure monitor may comprise any of the capacitive pressure sensors described herein. As a non-limiting example, the capacitive pressure sensor may comprise a first electrode layer; a second electrode layer, and a dielectric layer juxtaposed between the first and second electrode layers. In a preferred embodiment, when the sensor is in a resting configuration, an air gap is disposed between the first electrode layer and the second electrode layer, wherein when the sensor is compressed, a height of the air gap is reduced, thereby bringing the first electrode layer and the second electrode layer closer to each other and increasing a pressure sensitivity and capacitance of the sensor.

In some embodiments, the blood pressure monitor may be applied to an artery of the subject, such as the radial artery or another artery. In some embodiments, the blood pressure monitor may be calibrated to measure a beat-to-beat blood pressure. In some embodiments, the training set may comprise measurements from multiple patients. As a non-limiting example, the training set may comprise measurements from 10 s, 100 s, 1000 s, 10,000 s or more patients. According to one embodiment, the calibrated blood pressure monitor may be accurately used on a new patient without need for recalibration.

In some embodiments, the mechanical blood pressure signal may comprise a pulse waveform. In some embodiments, the additional biological input variables comprise sensor pressure, pulse rate, EKG data, accelerometer data, gyroscope data, magnetometer data, or hemodynamic monitoring data. In some embodiments, the method may additionally comprise subtracting out motion artifacts. As a non-limiting example, the motion artifacts may be subtracted out by including movement data in the training set. As a non-limiting example, movement data may be included in the training set by having the patients move in predetermined ways.

In one embodiment, the present invention features a calibrated mechanical, continuous blood pressure monitor. As a non-limiting example, the monitor may comprise: a capacitive pressure sensor, configured to allow for continuous monitoring of beat-to-beat blood pressure, and a calibration model generated by an artificial neural network (ANN) using a plurality of measurements from the capacitive pressure sensor. In some embodiments, the calibrated blood pressure monitor may be configured to provide accurate blood pressure measurement without additional data input.

In some embodiments, the plurality of measurements may be from a single patient or from multiple patients. In some embodiments the capacitive pressure sensor may be disposable or reusable. In some embodiments, the sensor may be configured to be attached to a skin surface of a patient. As a non-limiting example, the sensor may be attached over an artery of the patient. In a preferred embodiment, the monitor may comprise a single sensor. Alternatively, the multiple sensors may be used in conjunction.

In one embodiment, the present invention features a method of continuously monitoring a beat-to-beat blood pressure of a subject in need thereof. As a non-limiting example, the method may comprise: providing a calibrated mechanical, continuous blood pressure monitor: attaching the monitor to a forearm or wrist of the subject at a radial artery of the subject; measuring a mechanical blood pressure signal of the subject using the monitor; and interpreting the measured signal using a calibration model to determine an absolute blood pressure value. In some embodiments, the monitor may comprise a capacitive pressure sensor. In some embodiments, the method may be non-invasive. In some embodiments, calibration of the monitor may be done using an artificial neural network (ANN). In some embodiments, the monitor is attached to a skin surface of the subject by an adhesive or a cuff.

In other embodiments, the pressure sensor of the present invention may be applied onto other parts of the body, and is not limited to application on the forearm or wrist. For example, the sensor may be attached to the neck, upper arm, chest, leg, etc.

In still other embodiments, the present invention may be implemented in other applications that require pressure measurements, flow rates, etc. As a non-limiting embodiment, the pressure sensor may be used on structures such as pipes.

EXAMPLE

The following is a non-limiting example of the present invention. It is to be understood that said example is not intended to limit the present invention in any way. Equivalents or substitutes are within the scope of the present invention.

Experimental

Figure 2:
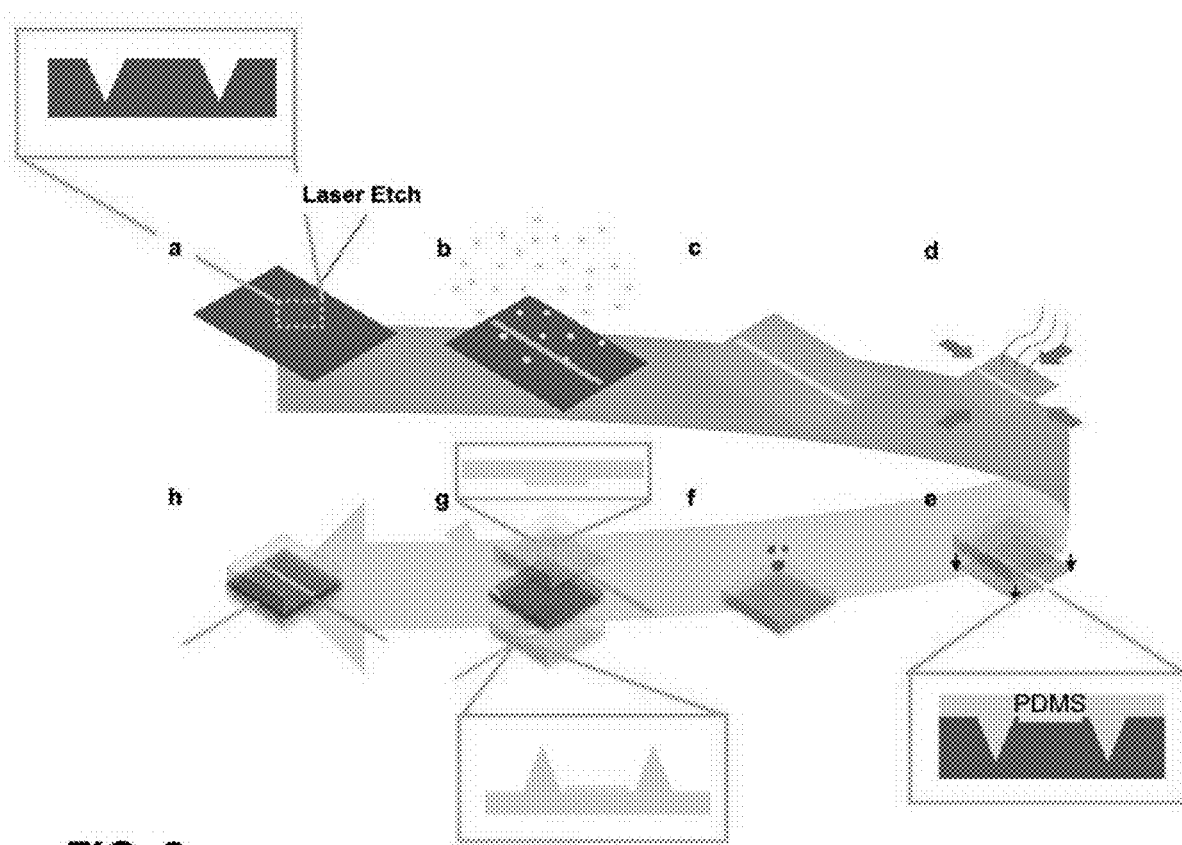
FIG. 2 illustrates a non-limiting embodiment of a fabrication process for producing soft capacitive pressure sensors. In step a), a laser cutter was used to etch into shadow mask and PS substrate. In step b), Au was sputtered through shadow mask onto PS substrate. In step c), the shadow mask is removed and in d) the PS substrate is heated to 140° C. to promote biaxial shrinking. In step e), after wAu is treated with MPTMS, silicone elastomer is spin coated over the substrate. Etched grooves are therefore molded. In step f), the substrate is placed in organic solvent to lift the wAu off the PS. In step g), after attaching electrical interconnects, electrode and dielectric layers are plasma bonded together to produce the final device in step h).

Fabrication of Capacitive Based Pressure Sensor:

The sensor was comprised of four layers: a wrinkled electrode, a dielectric layer, an air gap, and a wrinkled electrode with etched ridges. Referring to FIG. 2, to fabricate the electrodes, both processes began with rinsing a pre-stressed polystyrene (PS) substrate (Grafix Shrink Film KSF50-C, Grafix Arts, OH) with 70% ethanol. The sensor design was developed using AutoCAD (Autodesk, inc., Calif.), and patterned onto a shadow mask made with an adhesive polymer film (Grafix Frisket Film, Grafix Arts, OH) with a laser cutter (Universal Laser, AZ). Design was drawn such that the final electrode dimensions after shrinking was 2 mm in width and 15 mm in length. The Frisket film was first placed on top of the PS substrate, and the sensor design was then patterned onto the masked PS substrate. For the electrode with etched ridges, a higher power setting (0.5% Power, 3% Speed, 1000 PPI) was used to etch along the side of the electrode into the PS substrate. After both substrates were masked and patterned, a magnetron sputter coater (Q150R, Quorum Technologies, UK) was used to deposit 15 nm of Au onto each PS substrate.

Subsequently, the shadow mask was removed, and the sputtered substrate was placed into a convection oven at 140° C. to induce biaxial shrinking and wrinkling of the Au film. The shrunken samples were treated with 5 mM of 3-mercaptopropyl trimethoxysilane (95% MPTMS, Sigma Aldrich) in pure ethanol for 1 h. The samples were then rinsed with ethanol and dried with an air gun. Afterwards, polydimethylsiloxane (PDMS) (Sylgard 184 Silicone Elastomer Base, Dow Corning, MI) was poured over the MPTMS-treated Au film and spin coated at 300 rpm for 30 s with a final substrate thickness of approximately 0.5 mm. The samples were placed in a vacuum 30 minutes to remove bubbles and cured overnight in a convection oven at 60° C. The cured samples were then placed in a 75° acetone bath for 15 min to dissolve the PS substrate and lift the PDMS and wrinkle Au film off the PS. Afterwards, the residual PS was cleaned off of the wrinkled thin film by submerging the sensor in toluene for 2 min and rinsing with acetone. The samples were then air dried for overnight.

Colloidal silver liquid (Pelco Colloidal Silver Liquid, Ted Pella, CA) was used to interconnect the Au electrode to a wire and after drying, a resin was used encapsulate the interconnect interface. After the resin dried, polyimide tape was placed on the resin to further secure the interconnect to the electrode. Ecoflex® can only be plasma bonded to other silicones when Ecoflex® is cured on a PDMS substrate or chemically modified with other silicone elastomers. Therefore, a silicone elastomer Ecoflex®0030 (Smooth-On, PA) was first spin coated onto a cured PDMS layer with a spread step of 1000 rpm for 10 s, and spin coat step of 3000 RPM for 30 s for a final thickness of 15 µm. The elastomer was then placed into a 60° C. convection oven for 2 h to cure. Next, the cured elastomer was plasma bonded to the flat electrode at approximately 120 mTorr with ambient air for 40 s (PE-50, Plasma Etch, NV) and then placed in a 60° C. convection oven to promote chemical bonding. After removing the PDMS layer from the Ecoflex® layer, the flat electrode with the dielectric layer was then plasma bonded to the etched electrode to form the final capacitive based sensor. The sensor was placed into a convection oven at 60° C. to promote chemical bonding.

Flat Au electrodes (which served as the controls) were fabricated by patterning 90 nm Au onto PS substrate. The Au was treated with 5 mM MPTMS (95% MPTMS) in pure ethanol for 1 hr. PDMS was then spun coat at 300 RPM for 30 s on substrate and cured in the convection oven at 60° C. for 2 hrs. Acetone drops were placed on the PDMS to lift the Au from the PS substrate. After attaching electrical interconnects, Ecoflex® 0030 was spun coat on one electrode at 3000 RPM for 30 s and then cured in 60° C. convection oven for 2 hr. After curing, counter electrode was placed on top of the electrode with Ecoflex® dielectric layer. Surface area overlap of the electrodes were 2×2 mm².

Characterization:

A scanning electron microscope (SEM) (FEI Magellan 400 XHR) was used to characterize the wrinkle structures in the Au film. Pressure sensitivity was tested using a force gauge (Force Gauge Series 5, Mark-10, N.Y.) connected to a test stand (ESM303, Mark-10, N.Y.). The force gauge was placed slightly above the sensor, and then moved with a down speed of 1.1 mm per minute with a force probe diameter of 6 mm. Fiber glass probe was used to reduce fringe effects. The change in capacitance was collected as force was being applied and measured with an LCR meter (300 kHz) (E4980AL Precision LCR Meter, Keysight, CA). Data was collected using LabView and then processed using Matlab. An impedance analyzer (1 MHz, 500 mV) (4291B, Agilent, CA) was used to measure the signal response of the pressure sensor from cyclic and static loading applied by a custom-made linear actuator controlled by an Arduino. Distance information from the custom-made linear actuator was recorded with a linear potentiometer (Spectra Symbol, UT) using a National Instrument data acquisition system (USB-6003, Tex).

Beat-to-Beat Blood Pressure Methods:

The sensor was assembled onto a custom-made Velcro® band with a screw to incrementally apply pressure. Prior to attaching the sensor to the body, a Tegaderm® (3M Health Care, MN) strip was placed on the left wrist to promote compatibility between sensor and skin. The sensor was then attached and strapped down with custom made Velcro® band. The ClearSight® finger cuff was attached to the right index finger of the subject. Measurements between the pressure sensor and the ClearSight® device was measured simultaneously and subsequently analyzed in Matlab.

Statistical Analysis:

The sensor capacitance readings were acquired with a sampling frequency of approximately 56 Hz from the LCR meter (data points were timestamped with millisecond precision). All datasets were post-processed in Matlab and linearly interpolated to 200 Hz to match that of ClearSight®

(200 Hz). The interpolated data were then smoothed with a moving average filter of 5 data points.

As mentioned above, the ClearSight® segments the beat-to-beat blood pressure measurements by the number of cardiac cycles detected. Sections consisting of 70 beats were regarded as the most accurate and precise in measuring blood pressure. However, each of these sections only contained 69 full cardiac cycles, which were used for the analysis. Different breathing maneuvers were performed in four consecutive sections. Linear regression between the pressure sensor and ClearSight® for SBP, DSP, and MAP (n=69) for each subject and individual sections were obtained. The four sections for each subject were then combined and analyzed with linear regression (n=276).

Bland-Altman analysis was used to investigate agreement between the ClearSight® and the pressure sensor. The data from each subject were randomly split into two independent sets, where 75% of the data were used for creating the model and 25% were used to test the model. Linear regression models were built to predict SBP, DSP, and MAP values respectively (n=207). The remaining data for each subject (n=69) were then calibrated with the linear regression models. The mean bias and standard deviation were then calculated for all 9 subject tests combined for each SBP, DBP, and MAP parameter (n=621). Three consecutive cardiac cycles were averaged and analyzed similarly (n=207). Mean bias and standard deviation were calculated for all SBP, DBP, and MAP parameters combined for no cardiac cycle averaging (n=1863) and also for three consecutive cardiac cycle averaging (n=621).

Results

Sensor Fabrication

Soft capacitive pressure sensors comprised of two conductive parallel plates separated by a dielectric layer were fabricated using a thermally induced shrinking fabrication process (FIG. 2). Highly wrinkled structures in Au (wAu) thin films were formed when shrunk on polystyrene (PS) substrates. When these wrinkled thin film structures were transferred onto silicone elastomeric substrates, the wAu thin film demonstrated stretchability of up to 200% before electrical failure. Due to their mechanical robustness, these wAu electrodes were used as parallel plates (2×2 mm$^2$) in the capacitive pressure sensor. These wrinkled structures significantly improve mechanical robustness allowing wAu thin films of 15 nm thickness to be integrated into soft substrates and withstand thousands of cycles. Notably, these electrodes are capable of being supported on soft silicone substrates, including polydimethylsiloxane (PDMS), which are important to measure localized pressures. Many reported capacitive pressure sensors use stiff substrates such as polyethylene terephthalate (PET, E ~2.5 GPa) which are not as mechanically compatible to the human body as soft silicone elastomers, such as PDMS (E ~1 MPa). Stiff substrates may also potentially hinder spatial resolution of localized stress and negatively impact arterial pulse measurements.

Figure 5A:
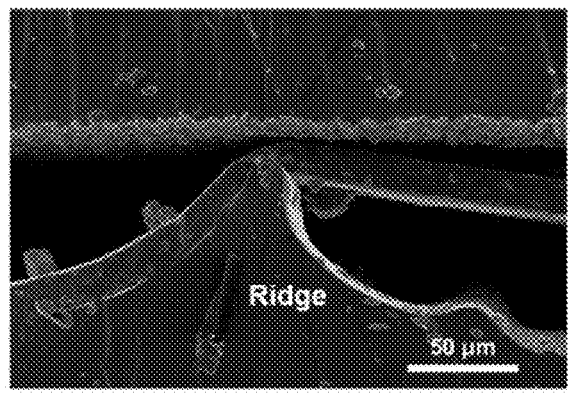
FIG. 5A shows an SEM image of the cross section of the micro ridge structure.
Figure 5B:
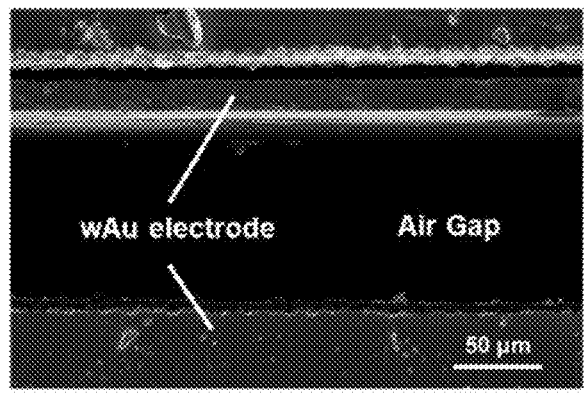
FIG. 5B shows an SEM image of the air gap present between the electrodes.
Figure 6:
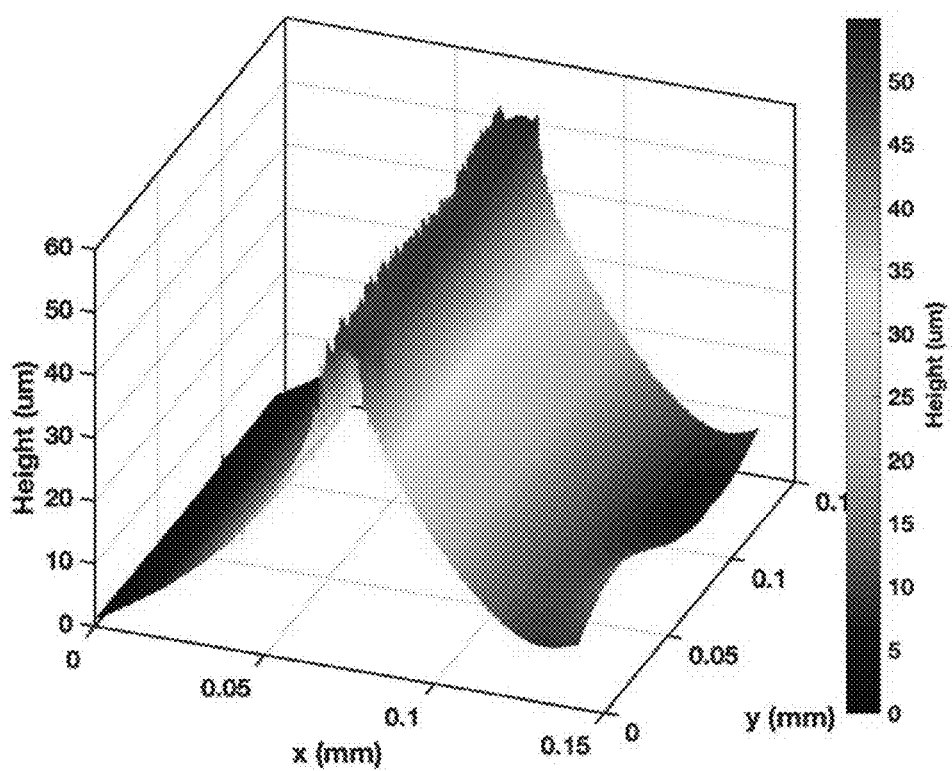
FIG. 6 shows a height profile of the PDMS elastic ridge formed during the PDMS molding process. An aspect ratio of ridge increases during the shrinking process.

A soft silicone elastomer, Ecoflex® (15 µm), was used as the soft dielectric layer between the parallel plates. Ecoflex® was used due to its soft mechanical properties (Shore hardness 00-30), as opposed to PDMS (Shore hardness A-48), to reduce the elastic resistance between the parallel plate electrodes to improve pressure sensitivity. In addition, micro-structured ridges were made by molding laser cut etched grooves in the PS substrate with PDMS. The micro-structured ridges were approximately 85 µm in height. 100 µM in width, and were spaced approximately 2 mm between each other located adjacent to the edge of the wrinkled thin film electrode which can be seen in FIG. 5A. The air gap size between the electrodes was approximately 130 µm in height seen in FIG. 5B. The ridge supported the counter electrode creating an air cavity within the dielectric layer.

When pressure was applied, the parallel plates were brought closer together leading to an increased capacitance. Due to the compression of the air cavity, the effective relative permittivity also increased closer to that of leading to larger changes in capacitance. This effect can be illustrated by Equation 2:

$$\frac{\Delta C}{C_o} = \frac{\varepsilon_o \varepsilon_r (A/d)}{\varepsilon_o \varepsilon_{ro} (A/d_o)} - 1 = \frac{\varepsilon_r d_o}{\varepsilon_{ro} d} - 1 \tag{2}$$

where $\varepsilon_{ro}$ is the relative permittivity before added pressure, and $\varepsilon_r$ is the relative permittivity after added pressure.

Electromechanical Characterization

The soft capacitive pressure sensor's electromechanical performance was evaluated by measuring pressure sensitivity which is defined by Equation 3:

$$S = \frac{\Delta C / C_o}{P} \tag{3}$$

where $\Delta C$ is the change in capacitance, $C_o$ is the initial capacitance, and P is pressure. The pressure sensitivity of the sensor was measured by applying force and measuring the change in capacitance. The force was applied over a 6 mm fiber glass probe tip attached to a force gauge. The fiber glass probe was used to reduce any fringe capacitance interference with the capacitive pressure sensor.

Figure 7A:
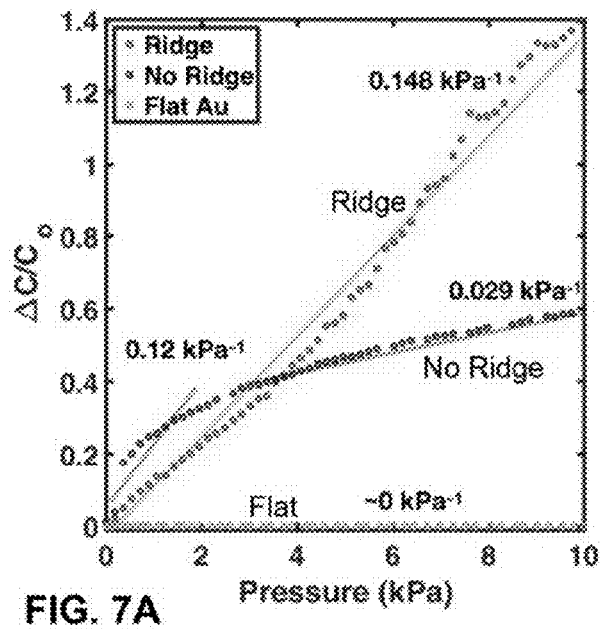
FIG. 7A shows a pressure sensitivity curve from 0-10 kPa of capacitive pressure sensor with ridge (red), no ridge (blue), and sensor made with flat Au electrodes (green).
Figure 8:
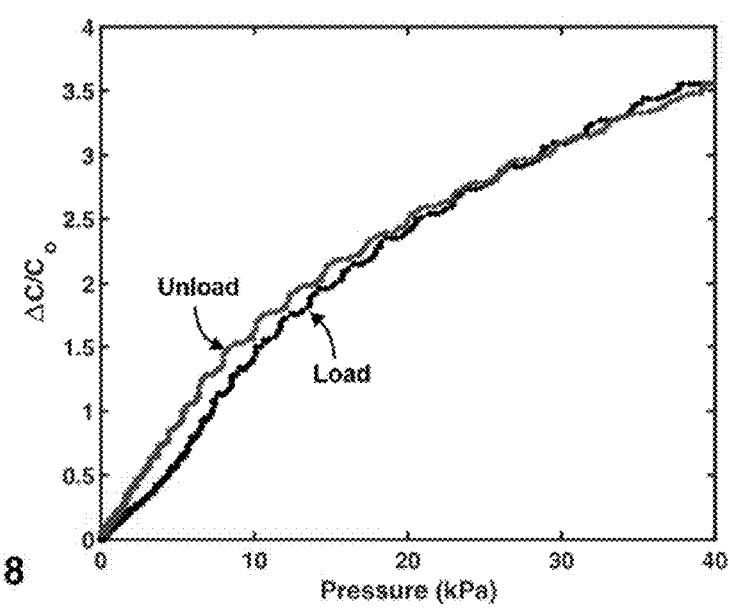
FIG. 8 is an inset of FIG. 7B, which illustrates the electromechanical response of the pressure sensor after loading and unloading 1 N of force (~40 kPa).

The pressure sensitivity of sensors with micro-structured ridges measured was 0.148 kPa$^{-1}$ between 0-10 kPa (FIG. 7A). A control of wrinkled electrodes with no micro-structured ridges was also tested. The capacitive pressure sensor with no micro ridges was characterized with a lower pressure sensitivity of 0.029 kPa$^{-1}$ between 3-10 kPa. However, the pressure sensitivity of the pressure sensors with no ridges displayed a pressure sensitivity of around 0.12 kPa$^{-1}$ in the 0-2 kPa range, which is comparable to the pressure sensor with the micro ridges. In this case, although there are no micro ridges to create an air cavity, small air gaps are still present due to the roughness of the wrinkled Au electrodes. However, these air gaps are completely compressed in the low-pressure regions resulting in lower pressure sensitivities when additional pressure is applied. Therefore, the micro-structured ridges allow soft capacitive pressure sensors to achieve high pressure sensitivities over a wide dynamic range. However, when the micro ridge size increases (190 µm height; 600 µm width), the pressure sensitivity decreased (FIG. 8). This decrease in pressure sensitivity can be attributed to the larger features that need to be compressed.

Capacitive pressure sensors with flat Au electrodes were fabricated to compare against wAu electrodes. Due to the brittleness of Au thin films on PDMS substrates, 90 nm of Au was used instead of 15 nm as it was not possible to transfer the 15 nm. The capacitive pressure sensors with flat Au electrodes displayed pressure sensitivities of ~0 kPa$^{-1}$ from 0-10 kPa (which had little to no air gap present). This suggests that the wAu electrodes provide mechanical robustness allowing for depositions of thin films of as low as 15 nm, and also display significantly higher pressure sensitivities compared to flat Au electrodes.

Figure 7B:
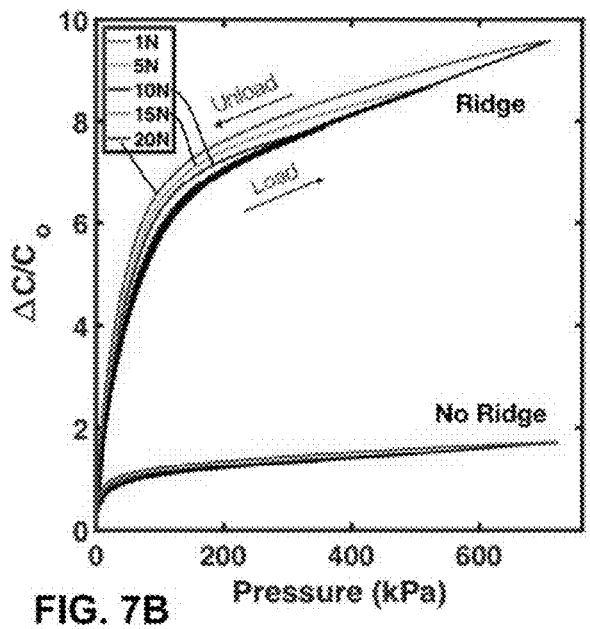
FIG. 7B shows a pressure sensitivity curve of the pressure sensor with the ridge versus with no ridge. Black lines indicate the loading, and the colored lines indicate the unloading. The amount of load that was applied prior to unloading is indicated by the colored lines in Newtons.

Larger pressure ranges were also investigated and compared between sensors with and without the micro-structured ridges. A mechanical load was first applied and then unloaded with 1 N (FIG. 8) displaying signs of hysteresis. This was then repeated with increasing loads from 1-20 N as seen in FIG. 7B. The electromechanical response of both conditions display characteristics of the Mullins effect, which states that the stress-strain curve depends on the magnitude of stress previously applied. As seen in FIG. 7B, the electromechanical response of the pressure sensor with micro ridges displayed higher pressure sensitivities over a wider dynamic range in comparison to the pressure sensor with no micro ridges.

Figure 9:
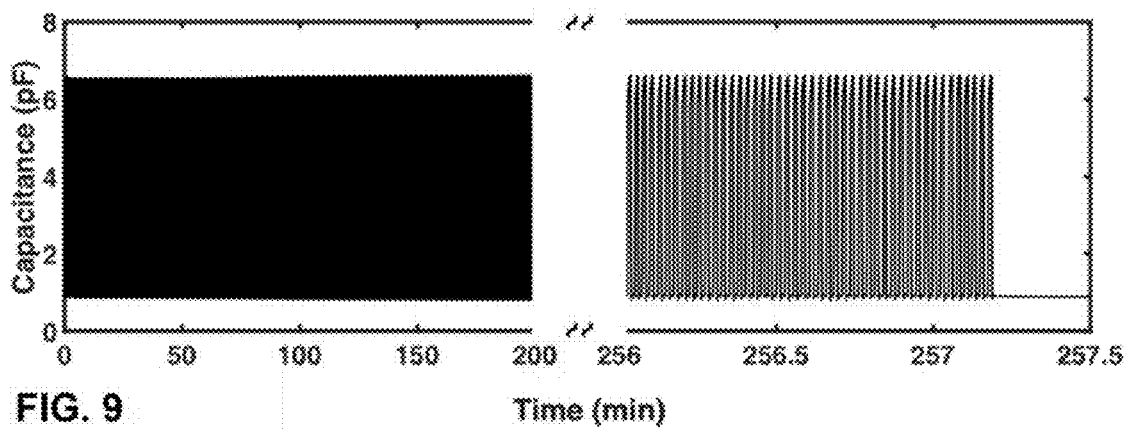
FIG. 9 shows a graph of the cyclic load of 25 kPa over 5000 cycles.
Figure 10A:
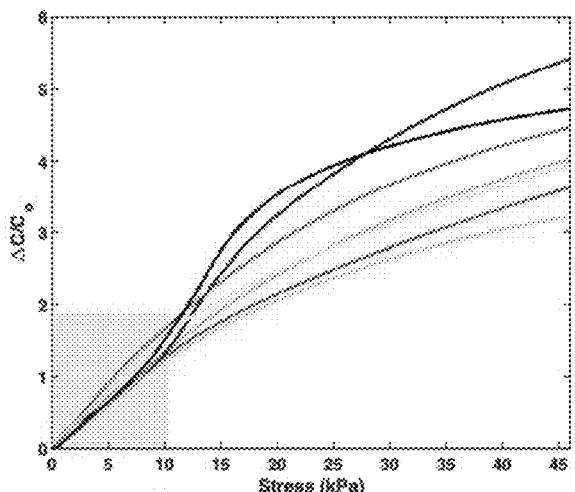
FIGS. 10A-10F show pressure sensitivity (PS) curves for soft capacitive pressure sensor.
Figure 10B:
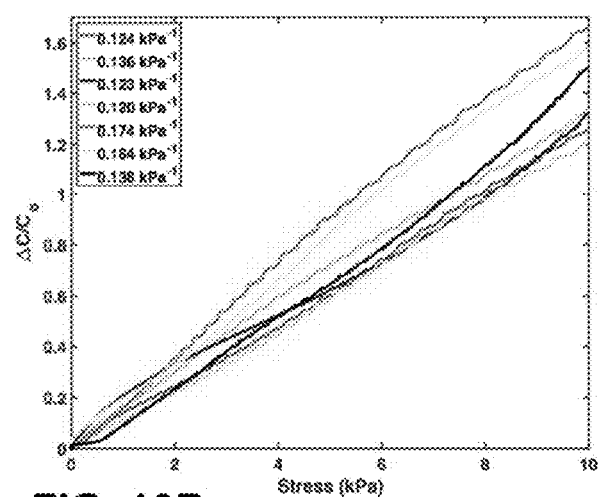
Figure 10C:
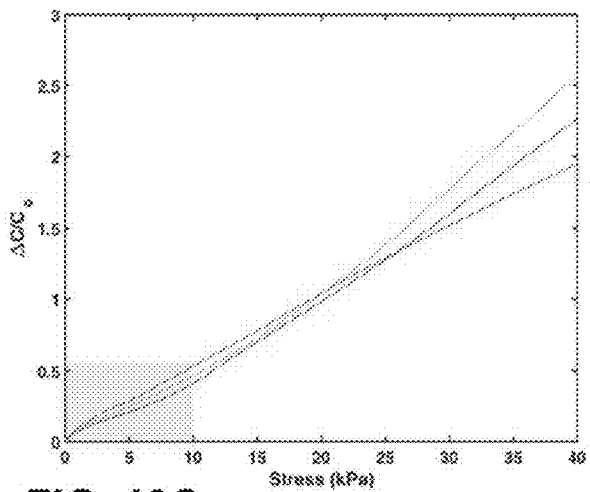
Figure 10D:
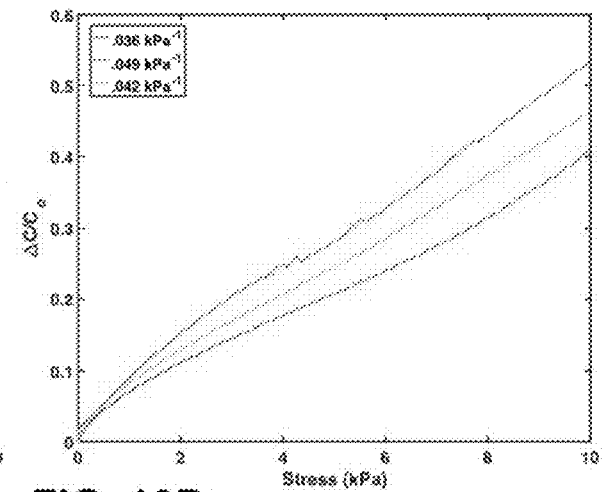
Figure 10E:
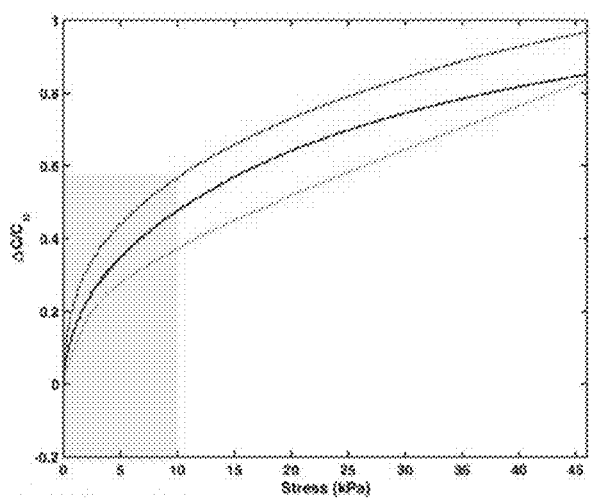
Figure 10F:
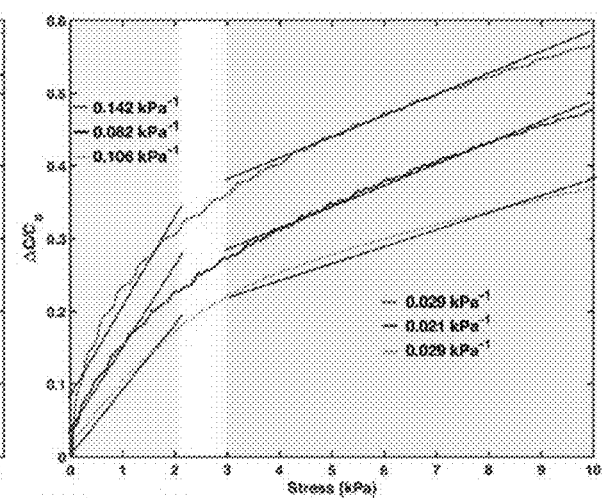

In addition, the electromechanical response to cyclical loading was analyzed as shown in FIG. 9. Approximately 25 kPa was applied to the pressure sensor for 5,000 cycles. The pressure sensor showed mechanical robustness to stress over a large number of cyclic loads. This demonstrates durability to cyclic mechanical loading which is necessary for continuous arterial pressure measurements.

Figure 11:
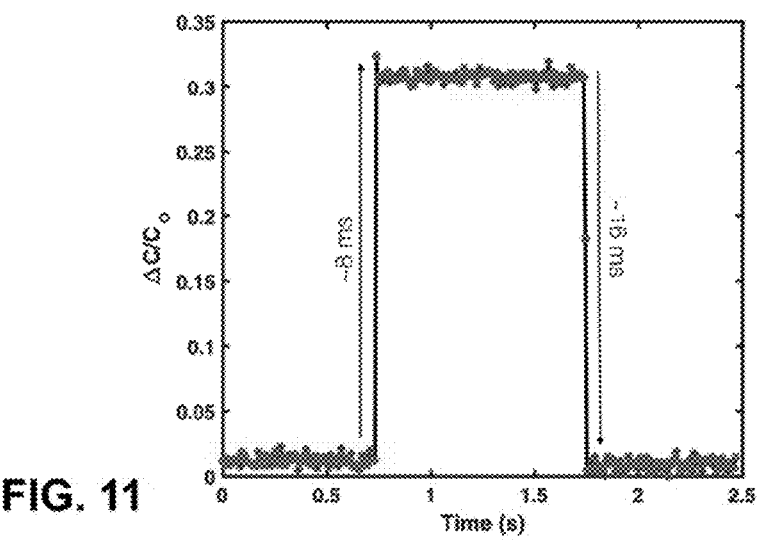
FIG. 11 shows a signal response after inducing an impulse of strain onto the pressure sensor. A small probe with approximately 2 mm diameter was attached to a linear actuator controlled by an Arduino to induce an impulse of strain (<1 ms).
Figure 12A:
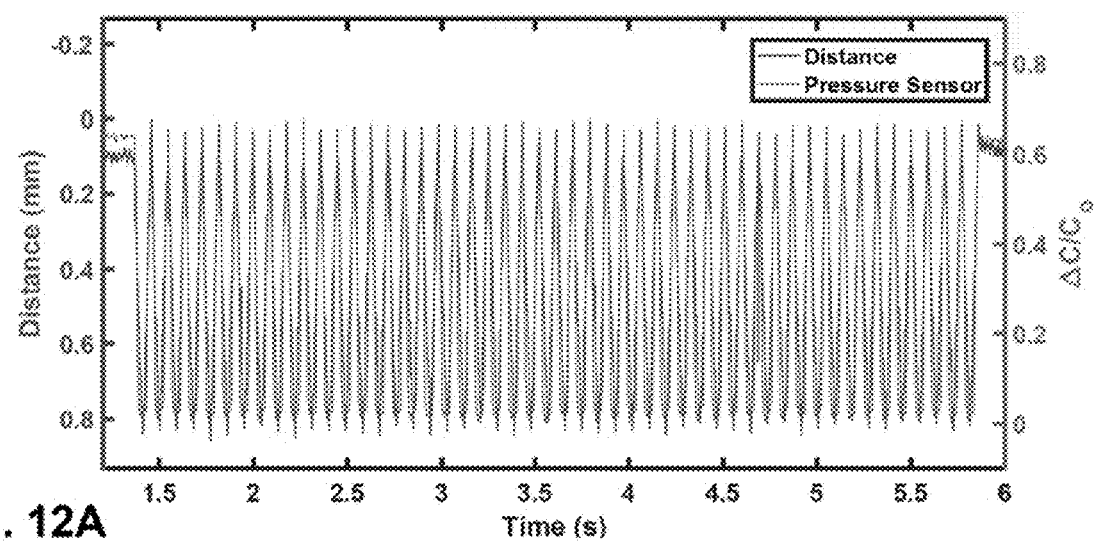
FIGS. 12A-12B show the result when a small probe with approximately 2 mm diameter was attached to a linear actuator controlled by an Arduino. The experiment started with pre-applied strain to sensor. Distance was measured such that probe is moving away from the sensor with increasing distance (larger changes of capacitance occur at smaller distances).
Figure 12B:
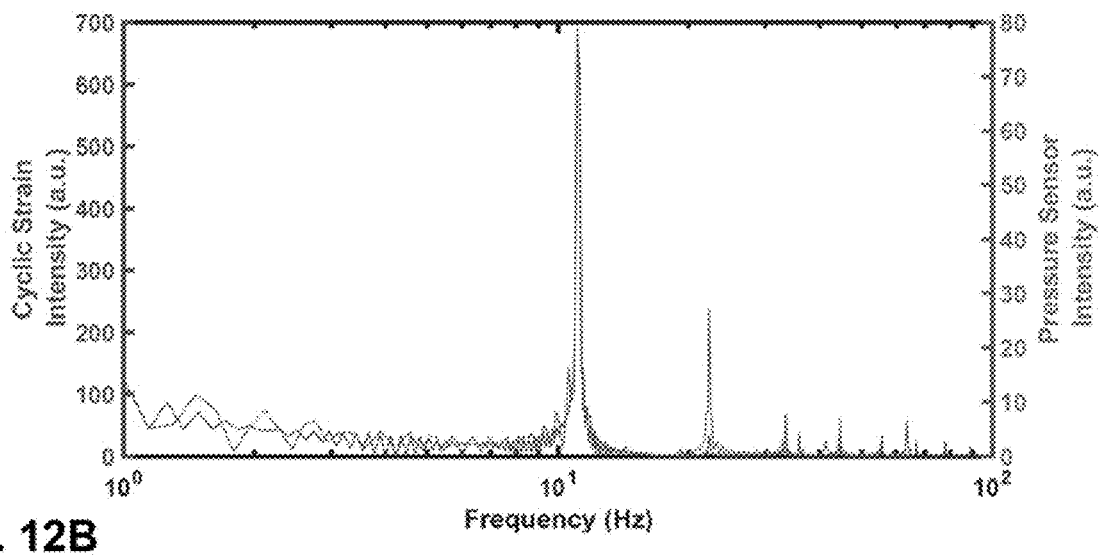

It is evident that incorporation of micro ridges improved pressure sensitivities of up to 5-fold within a wide dynamic range between 0-10 kPa. In addition, the mechanical robustness of the wrinkled structures allowed for deposition of significantly thinner electrodes making it more facile and rapid to fabricate. Reproducibility of these sensors are shown in FIGS. 10A-10F. In addition, response and relaxation times of the pressure sensor were measured. A probe with ~2 mm diameter was attached to a linear actuator which can be controlled by an Arduino. The pressure sensor displayed response times (<10 ms) and relaxation times (<17 ms) when applied with an impulse of strain (<1 ms) (FIG. 11). The pressure sensor was also capable of measuring cyclic strains of up to 10 Hz (FIGS. 12A-12B). Sampling measurement rate used for dynamic mechanical tests was 130 Hz (4291B, Agilent, CA).

Beat-to-Best Blood Pressure Monitoring
Experimental Setup for NIBP

As previously stated above, arterial tonometry is a method to quantify arterial pulse pressure using pressure sensors, it is possible to monitor arterial pulse pressure using soft capacitive pressure sensors as well. Accurate and precise measurement of the radial arterial pulse pressure can then be translated into beat-to-beat blood pressure for NIBP wearable applications.

To demonstrate beat-to-beat blood pressure monitoring, the sensors were applied to healthy subjects under approval from the institutional Review Board of the University of California (IRB no. 2016-2924). One soft capacitive pressure was tested on a total of 7 subjects to demonstrate robustness. Two additional soft capacitive sensors were tested on Subject 1 to demonstrate reproducibility. The pressure sensor was attached to the wrist over the radial artery. Afterwards, the subjects were told to keep their palm facing up and slightly hyperextended to help expose the radial artery on the surface of the skin. Subjects were sitting up with the pressure sensor close to heart level during these measurements. No allergic reactions or pain was reported by the subjects tested.

Figure 3A:
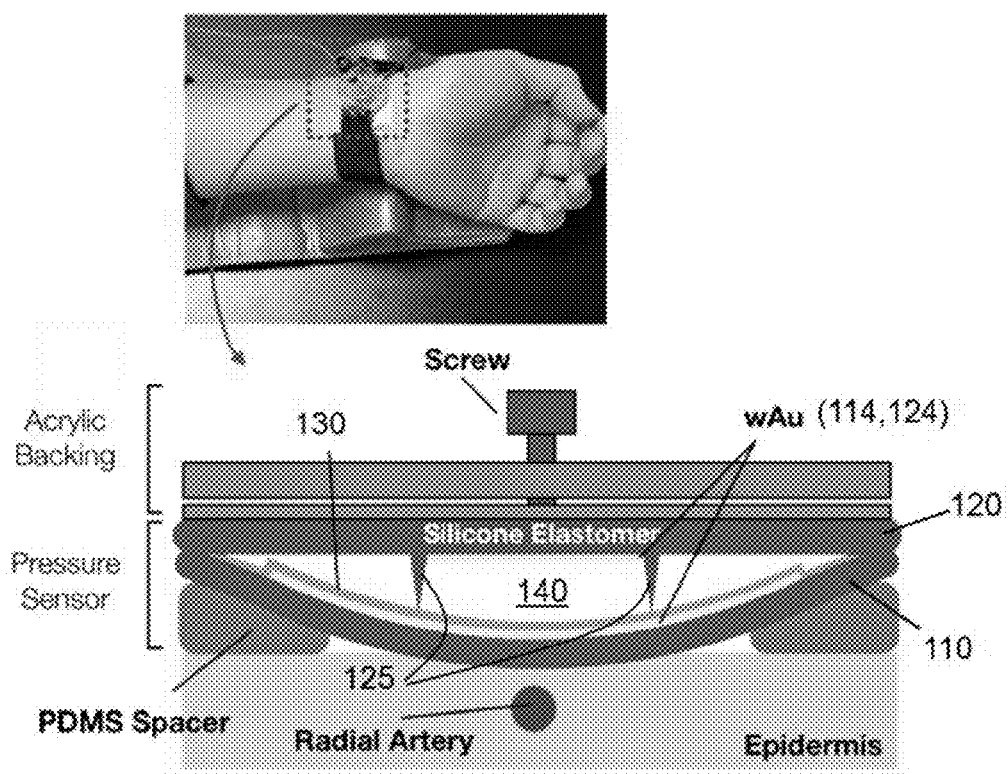
FIG. 3A-3B shows a schematic illustration of the pressure sensor when placed on the wrist above the radial artery. The pressure sensor is deformed as blood pulses through the radial artery. A screw is used to add incremental pressure to applanate the radial artery.
Figure 3B:
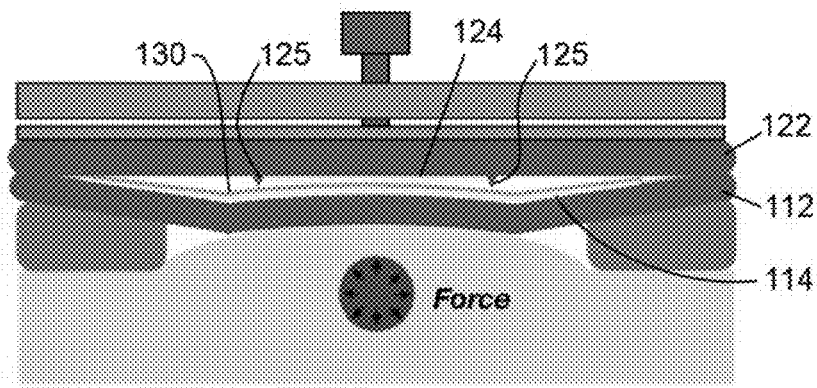
Figure 4:
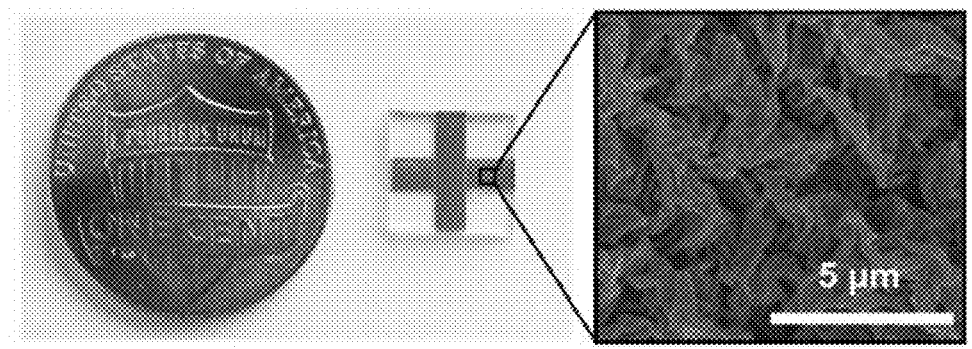
FIG. 4 shows an embodiment of the capacitive pressure sensor and a scanning electron microscope (SEM) image of the wAu.

For arterial pulse measurements, the pressure sensor was mounted onto an acrylic backing with a Velcro® strap. A screw was attached to the acrylic backing such that the acrylic backing can apply incremental pressure to applanate the radial artery. The incremental pressure increased the baseline capacitance of the capacitive pressure sensor. The schematic illustration for the pressure sensor device can be seen in FIGS. 3A-3B. Medical tape was also attached to the wrist to improve contact between pressure sensor and the human skin. Lastly, a PDMS spacer (250 μm) was also used between the pressure sensor and the epidermis to further compress the tissue and amplify the radial arterial pulse. As blood pressure increases in the radial artery, the radial artery expands which deforms the surrounding tissue subsequently deforming the pressure sensor. This pressure can be related to arterial blood pressure as long as the contact between the pressure sensor and the body is maintained consistent.

To evaluate the capacitive pressure sensor's ability to measure beat-to-beat blood pressure, the pressure sensor was compared against an FDA approved finger volume clamp device, ClearSight® (Edwards Lifesciences, Irvine, CA). The ClearSight® was attached to the right index finger of the subject. A photographic image showing where the devices were attached, can be seen in FIG. 14. Measurements were taken simultaneously where the pressure sensor measured the pressure exerted by the radial artery and the ClearSight® measured brachial arterial pressure. An example of the radial arterial pulse waveforms measured from the pressure sensor and the ClearSight® is presented in FIG. 16A. As seen in FIG. 16B, the quick response time and pressure sensitivity allowed for detection of the unique features in the radial arterial pulse waveform including the late systolic peak which is not easily discernible in the ClearSight® signal.

The parameters that were investigated included: systolic (SBP), diastolic (DBP), and the mean arterial pressures (MAP). These parameters are the most common when evaluating a person's cardiovascular health. The SBP is the blood pressure against the arterial walls when the heart has contracted, the DBP is the blood pressure against the arterial walls when the heart has relaxed, and the MAP is the average pressure throughout one cardiac cycle and can be calculated using Equation 4:

$$MAP=DBP+1/3(PP) \qquad (4)$$

where PP is the pulse pressure, which is equal to SBP minus DBP.

The arterial pulse can be palpated at many different regions on the human body. These arterial pulses have different waveforms as it propagates to different areas in the cardiovascular tree. As blood is pumped from the heart, to the peripheral arteries, the arterial pulse waveform is amplified due to narrowing of blood vessels. By measuring these arterial pulse pressures, it is possible to then use that information as a proxy to estimate arterial pulse pressure at different locations in the cardiovascular tree.

The ClearSight® measures the finger arterial pressure to estimate the brachial blood pressure. Extensive studies have evaluated the performance of the ClearSight® device in a wide population range and have shown satisfactory results in accurately and precisely measuring brachial arterial pressure when compared against the radial arterial catheter the gold standard for measuring beat-to-beat blood pressure. However, it is important to note that these studies have also shown variable results in patients, particularly when measuring systolic blood pressures.

Beat-to-Beat Blood Pressure Data Analysis

When the ClearSight® begins taking measurements, the ClearSight® measures 10 cardiac cycles before a calibration step begins. After self-evaluation in accuracy, the ClearSight® then measures 20 cardiac cycles and repeats the calibration step. The ClearSight® will continue to measure additional cardiac cycles until it has reached 70 cardiac cycles at which the ClearSight® is considered to be the most accurate and precise in measuring blood pressure. These epoch regions were where the capacitive pressure sensors were compared against the ClearSight®. In addition, subjects were asked to alternate between breathing deeply and normally after each subsequent 70 beat section respectively. By breathing deeply, it is possible to increase blood pressure due to slight heart compression from lung expansion. Subjects were asked to breathe deeply to assess the soft capacitive pressure sensor's ability to track larger changes in blood pressure.

Figure 16A:
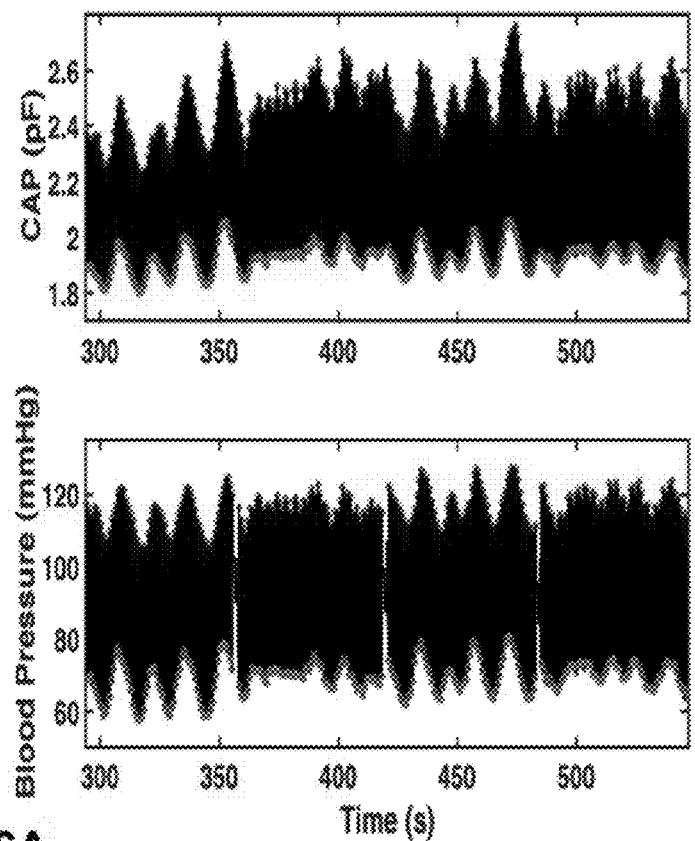
FIG. 16A shows an example of the four 70 beat sections from Subject 1 that were used to compare between the capacitive pressure sensor, and the ClearSight®. Arterial pulse waveforms are shown in black and highlighted in red indicate the SBP and DBP.
Figure 16B:
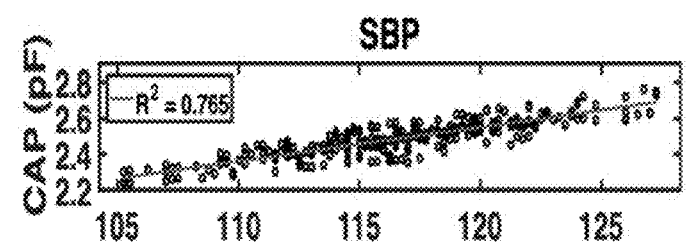
FIG. 16B shows linear regression analysis of SBP, DBP, and MAP between the pressure sensor and the ClearSight®.
Figure 16B:
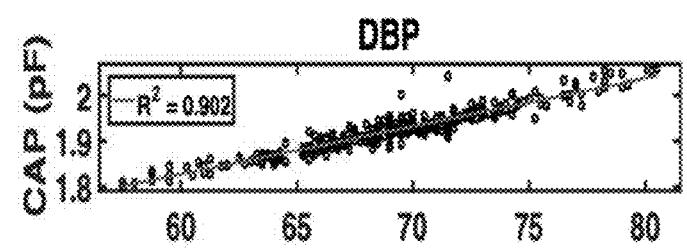
Figure 16B:
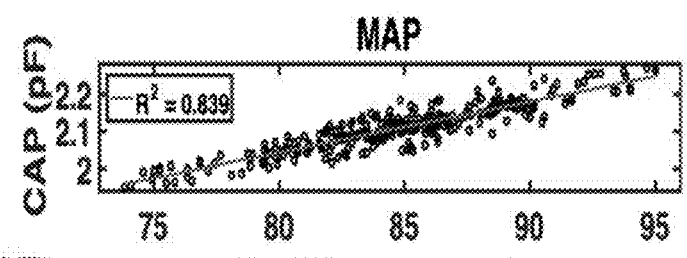

FIGS. 16A-16B illustrate the data collected for one subject. In FIG. 16A, qualitative analysis shows that the two devices measured similar trends in blood pressure. This is apparent during the deep breathing sections where low frequency blood pressure changes are reflected in both the pressure sensor and ClearSight®. The SBP, DBP, and MAP were subsequently plotted against each other and analyzed using linear regression as seen in FIG. 16B. The fit between the pressure sensor and ClearSight® device showed strong correlation with $R^2=0.765$ for SBP, $R^2=0.902$ for DBP, and $R^2=0.839$ for MAP. As stated earlier, the ClearSight® device has difficulties in measuring accurate and precise SBP values which may explain the lower $R^2$ between the pressure sensor and the ClearSight®.

The remaining subject data can be seen in the TABLES 1-3.

TABLE 1

Linear regression $R^2$ between the pressure sensor and Clearsight ® for SBP.

| Subject | Deep (1) | Normal (1) | Deep (2) | Normal (2) | Combined |
|---|---|---|---|---|---|
| 1a* | 0.741 | 0.601 | 0.815 | 0.915 | 0.765 |
| 2 | 0.824 | 0.769 | 0.827 | 0.639 | 0.754 |
| 3 | 0.520 | 0.798 | 0.854 | 0.767 | 0.662 |
| 4 | 0.650 | 0.815 | 0.720 | 0.886 | 0.578 |
| 5 | 0.755 | 0.235 | 0.317 | 0.469 | 0.554 |
| 6 | 0.429 | 0.500 | 0.866 | 0.722 | 0.477 |
| 7 | 0.733 | 0.743 | 0.619 | 0.289 | 0.536 |
| 1b* | 0.857 | 0.894 | 0.902 | 0.944 | 0.830 |
| 1c* | 0.856 | 0.818 | 0.922 | 0.775 | 0.673 |
| 1d** | — | — | — | — | — |

*Three different pressure sensors were tested.
**Data omitted due to loose interconnection.

TABLE 2

Linear regression $R^2$ between the pressure sensor and Clearsight ® for DBP.

| Subject | Deep (1) | Normal (1) | Deep (2) | Normal (2) | Combined |
|---|---|---|---|---|---|
| 1a* | 0.903 | 0.660 | 0.968 | 0.932 | 0.901 |
| 2 | 0.929 | 0.912 | 0.921 | 0.794 | 0.906 |
| 3 | 0.696 | 0.841 | 0.871 | 0.765 | 0.769 |
| 4 | 0.646 | 0.942 | 0.900 | 0.978 | 0.809 |
| 5 | 0.934 | 0.707 | 0.848 | 0.822 | 0.865 |
| 6 | 0.889 | 0.843 | 0.972 | 0.900 | 0.848 |
| 7 | 0.887 | 0.964 | 0 872 | 0.664 | 0.837 |
| 1b* | 0.931 | 0.880 | 0.907 | 0.945 | 0.871 |
| 1c* | 0.909 | 0.732 | 0.719 | 0.855 | 0.782 |
| 1d** | — | — | — | — | — |

*Different pressure sensors were tested.
**Data omitted due to loose interconnection.

TABLE 3

Linear regression $R^2$ between the pressure sensor and Clearsight ® for MAP.

| Subject | Deep (1) | Normal (1) | Deep (2) | Normal (2) | Combined |
|---|---|---|---|---|---|
| 1a* | 0.848 | 0.576 | 0.903 | 0.928 | 0.839 |
| 2 | 0.897 | 0.843 | 0.845 | 0.684 | 0.843 |
| 3 | 0.555 | 0.836 | 0.823 | 0.728 | 0.683 |
| 4 | 0.404 | 0.890 | 0.728 | 0.936 | 0.637 |
| 5 | 0.896 | 0.535 | 0.693 | 0.734 | 0.789 |
| 6 | 0.637 | 0.504 | 0.871 | 0.798 | 0.579 |
| 7 | 0.764 | 0.913 | 0 769 | 0.471 | 0.704 |
| 1b* | 0.878 | 0.893 | 0.890 | 0.944 | 0.847 |
| 1c* | 0.893 | 0.771 | 0.807 | 0.823 | 0.728 |
| 1d** | — | — | — | — | — |

Figure 17A:
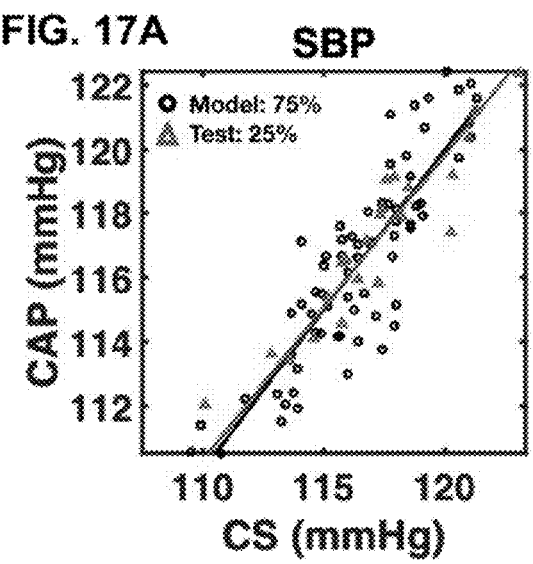
FIG. 17A shows an example of pressure sensor calibration model from Subject 1 for SBP.
Figure 17B:
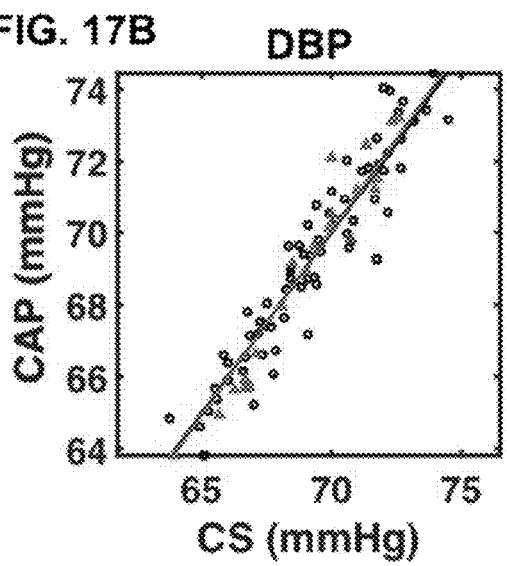
FIG. 17B shows an example of pressure sensor calibration model from Subject 1 for DBP.
Figure 17C:
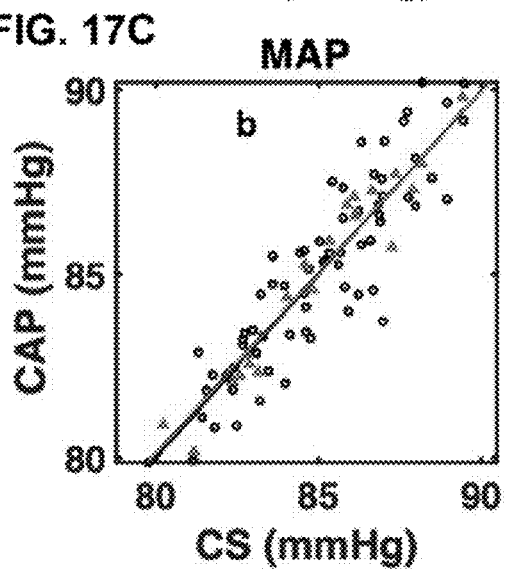
FIG. 17C shows an example of pressure sensor calibration model from Subject 1 for MBP.

*Three different pressure sensors were tested.
**Data omitted due to loose interconnection To further assess the accuracy and precision of the pressure sensor's ability to monitor beat-to-beat blood pressure, the pressure sensor was calibrated to the ClearSight® to generate a model for the pressure sensor and cross validated. To create the model, three consecutive cardiac cycles were first averaged together. After averaging, 75% of the data was randomly selected to generate a linear regression model for the pressure sensor. The remaining withheld dataset from the pressure sensor was converted to units of blood pressure millimeters of mercury (mmHg). An example of this calibration from one subject is shown in FIGS. 17A-17C.

Figure 17D:
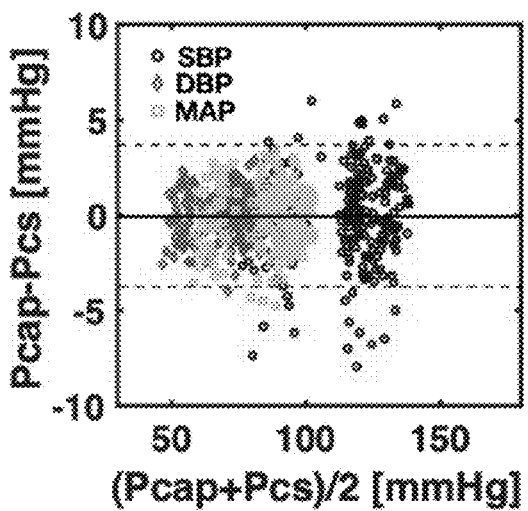
FIG. 17D shows a Bland-Altman plot for all subjects combined. The data includes the different sensors used on Subject 1 for a total of 9 independent tests. The dashed lines indicate two standard deviations and solid indicates mean bias.

Bland-Altman analysis was then used to assess the agreement in measurements of blood pressure between the pressure sensor and ClearSight®. Bland-Altman looks at the difference in blood pressures that were measured at the same time plotted against the average of the blood pressure measured at the same time. Larger differences would indicate larger disagreement between the two devices. As shown in FIG. 17D, all 7 subjects are compiled into one Bland-Altman plot including data sets from Subject 1 that was tested with two additional sensors. Mean bias and standard deviation calculated was −0.054±2.09 mmHg. The ISO 81060-2 set by the AAMI has indicated that a NIBP is deemed interchangeable with an arterial catheter if mean biases are less than 5 mmHg with standard deviations of less than 8 mmHg. The Bland-Altman analysis here shows that the mean bias and standard deviation are well below the requirements indicated by the ISO standards. TABLES 4-5 also show the mean bias and standard deviations calculated with no averaging of cardiac cycles which also show that the pressure sensor is well within the ISO standards. This suggests that the pressure sensor is highly accurate and precise in measuring blood pressure when calibrated to the ClearSight® device.

TABLE 4

Mean bias and standard deviation from Bland-Altman analysis.*

| Cardiac Cycle Averaging | Pairs | Mean Bias ± SD SBP | Mean Bias ± SD DBP | Mean Bias ± SD MAP |
|---|---|---|---|---|
| 1 | 621 | −0.194 ± 4.52 | −0.139 ± 1.99 | −0.166 ± 2.85 |
| 3 | 207 | −0.078 ± 2.86 | −0.029 ± 1.26 | −0.055 ± 1.84 |

*Bland-Altman analysis includes all tests from subject 1.

TABLE 5

Combined Bland-Altman analysis of SBP, DBP, and MAP parameters.*

| Cardiac Cycle Averaging | Pairs | Mean Bias ± SD Combined |
|---|---|---|
| 1 | 1,863 | −0.166 ± 3.29 |
| 3 | 621 | −0.054 ± 2.09 |

*Bland-Altman analysis includes all tests from subject 1.

The soft capacitive pressure sensors of the present invention may be utilized for radial arterial tonometry applications. Consistent measurements of the arterial pulse pressure allowed for tracking and detecting nominal changes in SBP, DBP, and MAP pressures. Correlation between the ClearSight device show promising results for potential ambulatory beat-to-beat NIBP monitoring. The capabilities to accurately monitor a wide range of pressures are enabled by the electromechanical properties of the pressure sensor. In addition, the quick response times and wide dynamic range of the capacitive pressure sensors allowed for detecting the radial arterial pulse waveform with high fidelity, thereby allowing for accurate and precise measurements of blood pressure that are essential for monitoring acute cardiovascular events.

In further embodiments, the present invention provides a facile method to develop a soft capacitive pressure sensor that has favorable electromechanical properties for measuring arterial pulsatile blood flow. By utilizing soft, highly wrinkled thin film electrodes, it was possible to fabricate soft pressure sensors with a large dynamic range that can couple effectively with the human body for the quantification of localized and subtle pressure. The sensors also demonstrated sufficient pressure sensitivities, quick response times, as well as mechanical robustness to cyclic loads.

Blood Pressure Calibration with Pulse Transit Time (PTT)

Pulse pressure measurements taken with the pressure sensor of the present invention is highly correlated with the blood pressure measurements taken with the ClearSight®. However, there is still a need to calibrate the pulse pressure measurements taken with the pressure sensors to absolute blood pressure without continuous dependence on the ClearSight®.

There are two notable methods that can be used to calibrate the pressure sensors to measure absolute blood pressure. One method requires the use of a traditional oscillometric arm cuff to calibrate the systolic and diastolic blood pressures. Oscillometric arm cuffs calculate systolic and diastolic blood pressures over a set period of time during inflation and deflation of the arm cuff. Even though this measurement does not provide beat-to-beat blood pressure, the values calculated by the oscillometric arm cuff can be used to calibrate the pressure sensor to a blood pressure baseline.

Figure 18:
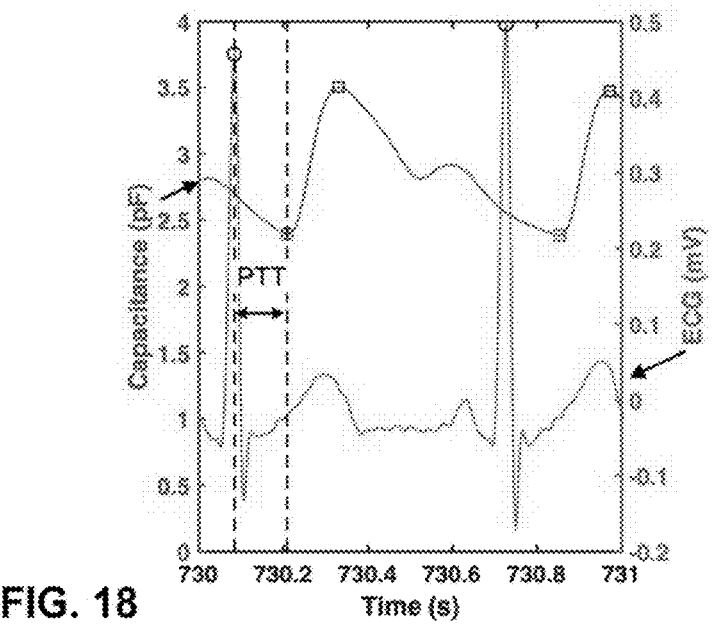
FIG. 18 shows a pulse transit time (PTT) measurement method with ECG (mV) and pressure sensor (pF) placed at the radial artery.
Figure 19:
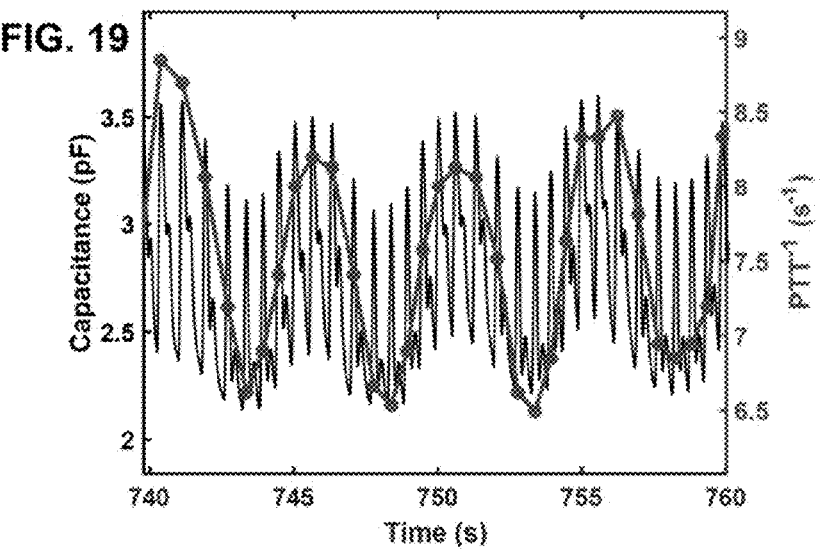
FIG. 19 shows $PTT^1$ (solid circle-line) measured using ECG has similar trends in blood pressure variability measured by the pressure sensor.

Another method involves the use of pulse transit time (PTT). PTT is the duration of how quickly a pulse wave has traveled from one, arterial location to another. The time the pulse wave travels is directly related to blood pressure. For example, the faster the pulse wave travels the higher the blood pressure is and vice versa. PTT can be measured by using an ECG and a pressure sensor located at a peripheral artery (i.e. radial artery). The ECG provides the moment the heart has contracted and the pressure sensor provides information on how long the pulse took to travel to a peripheral artery. More specifically, PTT is the time between the R-peak of the ECG and the corresponding diastolic peak measured with the pressure sensor (FIG. 18). PTT can also be measured using two peripheral sensors and measuring the time a pulse travels from one sensor to the next. Research has shown measuring pulse wave in the peripheral arteries as opposed to using ECG provides better correlations to blood pressure. This can be accomplished by measuring with two pressure sensors where one is placed on the radial artery and another placed on the brachial artery. Note that PTT can only provide absolute blood pressure values and does not provide any other information of the pulse wave (e.g. augmentation index) (FIG. 19).

Figure 20A:
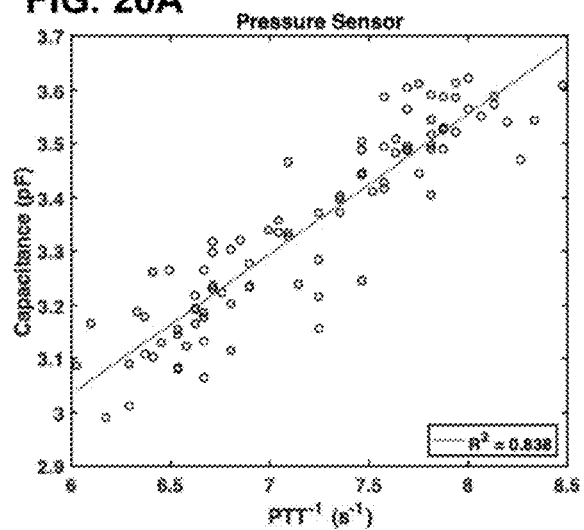
FIGS. 20A-20B show $PTT^1$ correlation to pressure sensor and ClearSight® respectively.
Figure 20B:
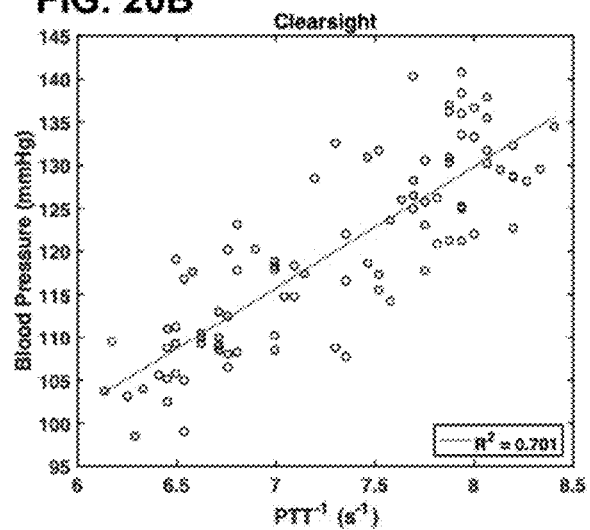
Figure 20C:
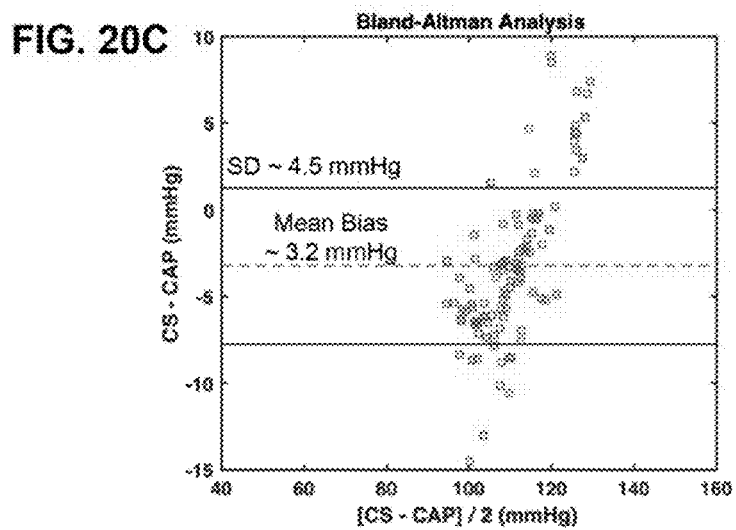
FIG. 20C shows 60 seconds of pressure sensor data measured at a different time that was then calibrated using the PTT model generated from the ClearSight®. Bland-Altman analysis of the systolic peaks show mean bias and standard deviation within ISO standards for FDA approval.
Figure 21:
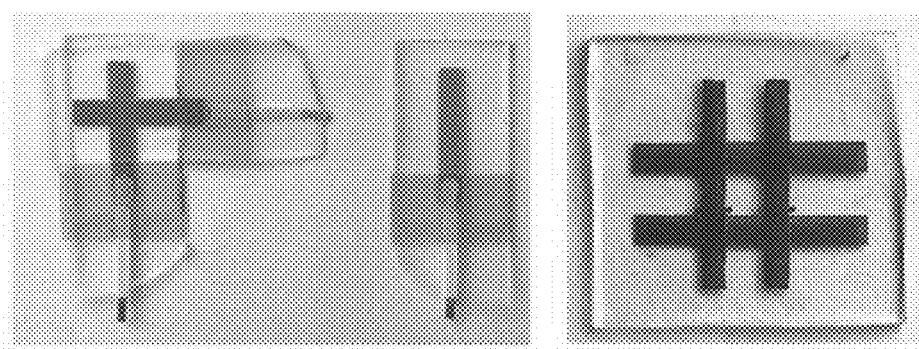
FIG. 21 shows, from left to right, a plasma bonded capacitive pressure sensor, an individual electrode, and a 4×4 sensing grid of a capacitive pressure sensor
Figure 22A:
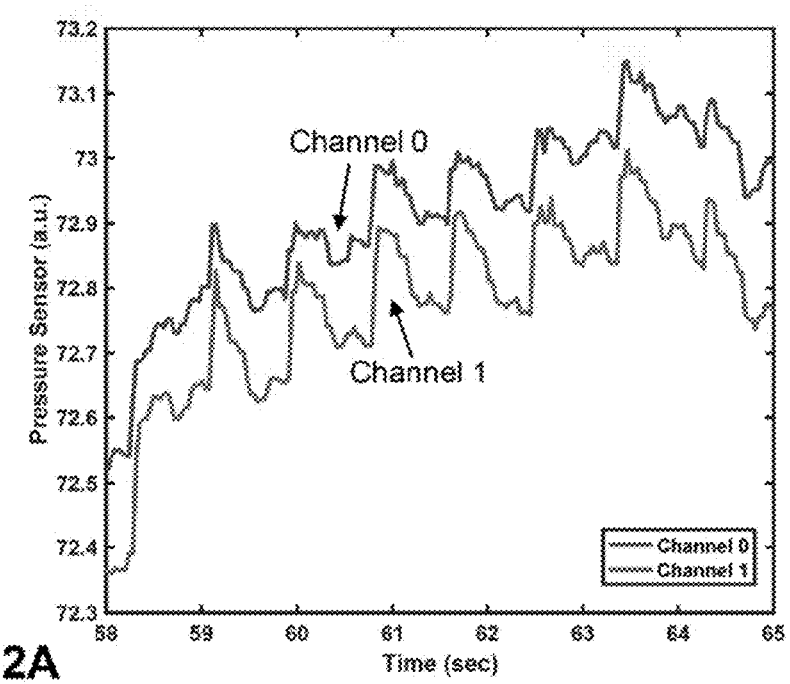
FIG. 22A shows pulse measurements with two sensing areas.
Figure 22B:
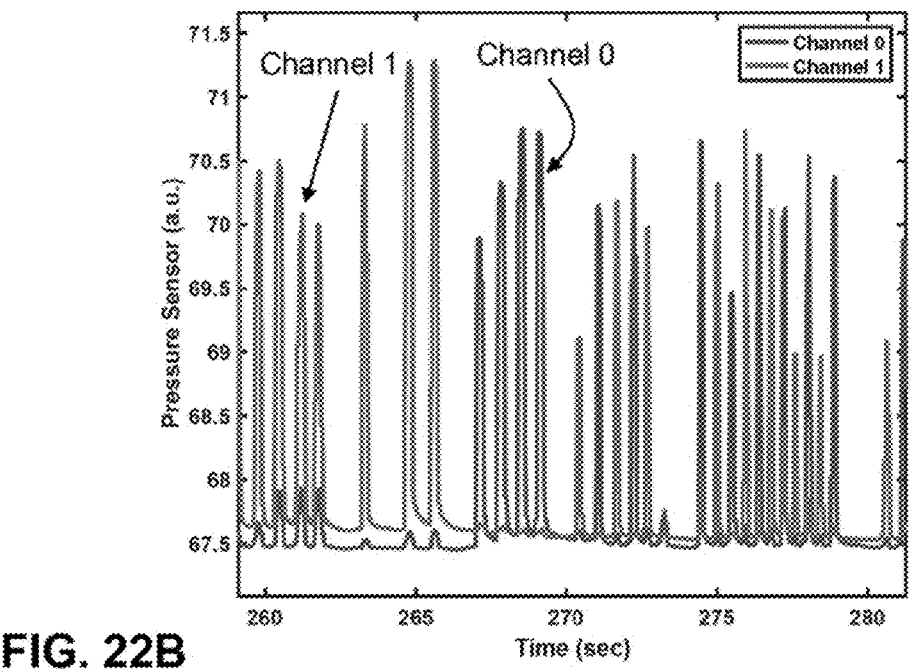
FIG. 22B demonstrates the capabilities of the sensor to spatially resolve pressures in different locations on the same sensor. Data acquisition was performed using Texas Instruments FDC 2214 EVM.

PTT is a subject dependent parameter and requires calibration to blood pressure. This can be accomplished by calibrating to a traditional arm cuff as previously mentioned (ClearSight® can also be used to calibrate the PTT). The PTT model can then be used from months to years until the PTT model requires recalibration. Once the PIT model is calibrated, the PTT model can then subsequently used to calibrate the pressure sensor (FIGS. 20A-20C). The benefit of calibrating the pressure sensor to the PTT model is the feedback mechanism to calibrate the pressure sensor to blood pressure after large movements, or when taking the pressure sensor on and off.

As used herein, the term "about" refers to plus or minus 10% of the referenced number.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A capacitive pressure sensor (100) comprising:
    a. a first electrode layer (110);
    b. a second electrode layer (120);
    c. a dielectric layer (130) disposed on the first electrode layer (110) such that the dielectric layer (130) is between the first and second electrode layers (110, 120);
    d. a plurality of elastic structures (125) projecting from the second electrode layer (120) toward the dielectric layer (130) and first electrode layer (110), wherein the plurality of elastic structures (125) creates an air gap (140) that separates the first electrode layer (110) and the second electrode layer (120); and
    e. a conductive metallic film (124) disposed between the plurality of elastic structures (125);
    wherein when the sensor (100) is in a resting configuration, the air gap (140) is disposed between the first electrode layer (110) and the second electrode layer (120), wherein the air gap (140) functions as a second dielectric layer, wherein when the sensor (100) is compressed, the first electrode layer (110) and the second electrode layer (120) are brought closer to each other, thereby reducing a height of the air gap and increasing a pressure sensitivity and capacitance of the sensor.

2. The sensor (100) of claim 1, wherein the first electrode layer (110) comprises an elastomer layer (112) and a conductive metallic film (114) disposed on the elastomer layer (112), wherein the conductive metallic film (114) is between the elastomer layer (112) and the dielectric layer (130).

3. The sensor (100) of claim 2, wherein the second electrode layer (120) comprises an elastomer layer (122) and the conductive metallic film (124) disposed on the elastomer layer (122).

4. The sensor (100) of claim 3, wherein the elastomer layers (112, 122) comprise polydimethylsiloxane or polyurethane.

5. The sensor (100) of 4, wherein the conductive metallic films (114, 124) comprise carbon nanotubes or wrinkled thin films of gold, silver, copper, or aluminum.

6. The sensor (100) of claim 1, wherein the dielectric layer (130) comprises a silicone elastomer, lead zirconate titanate, barium titanate, polyvinylidene fluoride, or an oxide of zirconia, titania, or silica.

7. The sensor (100) of claim 1, wherein a pressure sensitivity of the sensor is about 0.1 kPa$^{-1}$ to about 0.2 kPa$^{-1}$ in a pressure range between 0-10 kPa.

8. The sensor (100) of claim 1, wherein a response time of the sensor is less than about 20 ms.

9. A method of monitoring blood pressure in a subject, said method comprising:
  a. providing a capacitive pressure sensor (100) according to claim 1;
  b. attaching the sensor (100) to a wrist of the subject at the radial artery;
  c. measuring a blood pressure signal of the subject using the sensor (100), wherein pulsing of the radial artery causes compression of the sensor, wherein the sensor (100) detects the blood pressure signal corresponding to the radial artery pulses; and
  d. determining an absolute blood pressure value from the measured signal using a calibration model.

10. The method of claim 9, wherein the blood pressure is monitored beat to beat.

11. The method of claim 9 further comprising calibrating the capacitive pressure sensor (100) using an artificial neural network (ANN), comprising:
  a. measuring a plurality of blood pressure signals from the subject;
  b. measuring one or more biological input variables from the subject;
  c. combining the measured blood pressure signals and the biological input variables to form a training set; and
  d. training the ANN using the training set to generate the calibration model.

12. The method of claim 11, wherein the training set comprises measurements of blood pressure signals and one or more biological input variables from multiple subjects.

13. The method of claim 11, wherein the one or more biological input variables comprise sensor pressure, pulse rate, EKG data, accelerometer data, gyroscope data, magnetometer data, or hemodynamic monitoring data.

14. The method of claim 11 further comprising subtracting out motion artifacts by including movement data in the training set.

* * * * *